(12) United States Patent
Saigo et al.

(10) Patent No.: US 11,379,983 B2
(45) Date of Patent: Jul. 5, 2022

(54) ANALYSIS DEVICE, ANALYSIS PROGRAM, AND ANALYSIS METHOD

(71) Applicants: NIKON CORPORATION, Tokyo (JP); The University of Tokyo, Tokyo (JP)

(72) Inventors: Takuro Saigo, Tokyo (JP); Shoko Yamasaki, Tokyo (JP); Masayuki Murata, Tokyo (JP); Fumi Kano, Tokyo (JP); Yoshiyuki Noguchi, Tokyo (JP)

(73) Assignees: NIKON CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 216 days.

(21) Appl. No.: 16/623,003

(22) PCT Filed: Jun. 23, 2017

(86) PCT No.: PCT/JP2017/023135
§ 371 (c)(1),
(2) Date: Dec. 16, 2019

(87) PCT Pub. No.: WO2018/235251
PCT Pub. Date: Dec. 27, 2018

(65) Prior Publication Data
US 2020/0410682 A1    Dec. 31, 2020

(51) Int. Cl.
*G06T 7/00* (2017.01)
*G01N 15/10* (2006.01)
*G06V 20/69* (2022.01)

(52) U.S. Cl.
CPC ....... *G06T 7/0016* (2013.01); *G01N 15/1056* (2013.01); *G06V 20/693* (2022.01);
(Continued)

(58) Field of Classification Search
CPC ......... G06T 7/0016; G06T 2207/10056; G06T 2207/30024; G01N 15/1056;
(Continued)

(56) References Cited

U.S. PATENT DOCUMENTS 9,280,698 B2    3/2016  Kll et al.
2011/0091994 A1    4/2011  Lotteau
2014/0154266 A1    6/2014  Narain et al.

FOREIGN PATENT DOCUMENTS

JP    2009-139336 A    6/2009
JP    2011-517779 A    6/2011
(Continued)

OTHER PUBLICATIONS

Oct. 20, 2020 Office Action issued in Japanese Patent Application No. 2019-524816.
(Continued)

*Primary Examiner* — Michael R Neff
(74) *Attorney, Agent, or Firm* — Oliff PLC

(57) ABSTRACT

An analysis device configured to analyze an attribute of a correlation between responses with respect to a stimulus to a first subcellular component that is a subcellular component of a cell and a second subcellular component different from the first subcellular component, the analysis device including an attribute analysis unit that analyzes the attribute of the correlation between the first subcellular component and the second subcellular component based on a first change in a feature value of the second subcellular component with respect to the stimulus in a state a function of the first subcellular component is suppressed and a second change in a feature value of the second subcellular component with respect to the stimulus in a state the function of the first subcellular component is not suppressed.

13 Claims, 21 Drawing Sheets

(52) U.S. Cl.
CPC .......... *G06V 20/695* (2022.01); *G06V 20/698* (2022.01); *G01N 2015/1006* (2013.01); *G06T 2207/10056* (2013.01); *G06T 2207/30024* (2013.01)

(58) Field of Classification Search
CPC ....... G01N 2015/1006; G06K 9/00134; G06K 9/0014; G06K 9/00147
USPC ........................................................ 382/133
See application file for complete search history.

(56) References Cited

FOREIGN PATENT DOCUMENTS

| | | |
|---|---|---|
| JP | 2013-043862 A | 3/2013 |
| JP | 2015-520170 A | 7/2015 |
| WO | 2009/127693 A1 | 10/2009 |
| WO | 2009/127913 A1 | 10/2009 |
| WO | 2013/177535 A2 | 11/2013 |

OTHER PUBLICATIONS

Sep. 19, 2017 International Search Report issued in International Patent Application No. PCT/JP2017/023135.
Sep. 19, 2017 Written Opinion issued in International Patent Application No. PCT/JP2017/023135.
Jerome Friedman et al., "Sparse inverse covariance estimation with the graphic lasso," Biostatistics, (2008), 9, 3, pp. 432-441.
Apr. 27, 2021 Office Action issued in Japanese Patent Application No. 2019-524816.
Jan. 18, 2022 Office Action issued in Japanese Patent Application No. 2019-524816.

FIG. 4

| FOCUSED PROTEIN "A" | | (1) NO INHIBITION | (2) WITH INHIBITION | (3) COMPARISON BETWEEN NO AND WITH INHIBITION | | (4) | | (5) | | (6) NO INHIBITION | | (7) CONCLUSION OF RESULT |
|---|---|---|---|---|---|---|---|---|---|---|---|---|
| | | RESULT | RESULT | B-B CORRELATION | RESULT | B-B SIGNIFICANT DIFFERENCE | RESULT | DIFFERENCE BETWEEN B-B | RESULT | A-B CORRELATION | RESULT | CONCLUSION |
| | B SIGNAL | B SIGNAL | | | | | | | | | | |
| YES | WITH RESPONSE | | WITH RESPONSE UNDER INHIBITION | POSITIVE | SAME B-B RESPONSE | YES | DOWNSTREAM | B1 > B2 | ODDLY ACTIVATED | HIGH | DIRECT | ODDLY AND DIRECTLY ACTIVATED |
| | | | | | | | | | | LOW | INDIRECT | ODDLY AND INDIRECTLY ACTIVATED |
| | | | | | | | | B2 > B1 | ODDLY SUPPRESSED | HIGH | DIRECT | ODDLY AND DIRECTLY SUPPRESSED |
| | | | | | | | | | | LOW | INDIRECT | ODDLY AND INDIRECTLY SUPPRESSED |
| | | | | | | NO | NON-DOWNSTREAM | | | HIGH | HIGH POSSIBILITY OF BEING UPSTREAM | HIGH POSSIBILITY OF BEING UPSTREAM |
| | | | | | | | | | | LOW | NOT DOWNSTREAM | NOT DOWNSTREAM |
| | | | | NEGATIVE | OPPOSITE B-B RESPONSE | | | B1 > B2 | REVERSE ACTIVATION | HIGH | DIRECT | DIRECT REVERSE ACTIVATION |
| | | | | | | | | | | LOW | INDIRECT | INDIRECT REVERSE ACTIVATION |
| | | | | | | | | B2 > B1 | REVERSE SUPPRESSION | HIGH | DIRECT | DIRECT REVERSE SUPPRESSION |
| | | | | | | | | | | LOW | INDIRECT | INDIRECT REVERSE SUPPRESSION |
| | | | | NO | DIFFERENT B-B RESPONSE | | | | | | | ADJUSTMENT |
| NO | WITHOUT RESPONSE | | YES ACTIVATION | | | | | | | | | ACTIVATION |
| | | | NO SUPPRESSION | | | | | | | | | SUPPRESSION |
| | | | NO NO RESPONSE | | | | | | | | | NO RESPONSE |
| | | TB1 | | TB2 | | TB3 | | TB4 | | TB5 | | TBR |

NO STIMULUS (NO INDUCTION)

| Item | pValue | EffectSize |
|------|--------|------------|
| P1.m1 | 0.1044 | 0.043 |
| P1.m2 | 0.0002 | 0.202 |
| P2.m1 | 0.2738 | 0.128 |
| ... | | |
| PN.mx | 0.0045 | 0.021 |
| | | Max=0.202 |

WITH INDUCTION

| Item | pValue | EffectSize | Signal |
|------|--------|------------|--------|
| P1.m1 | 0.0044 | 0.121 | WITHOUT SIGNAL |
| P1.m2 | 0.0002 | 0.216 | WITH SIGNAL |
| P1.m3 | 0.2738 | 0.012 | WITHOUT SIGNAL |
| P2.m1 | 0.0045 | 0.428 | WITH SIGNAL |
| ... | | | |

FIG. 9A

CHECK WHETHER THERE IS SIGNAL:
COMPARISON AMONG MULTIPLE GROUPS,
COMPARISON AMONG ALL TIMES

| Item | pValue | EffectSize | Signal |
|---|---|---|---|
| B1 | 0.002 | 0.012 | WITHOUT SIGNAL |
| B2 | 0.102 | 0.030 | WITHOUT SIGNAL |
| B3 | 0.012 | 0.456 | WITH SIGNAL |

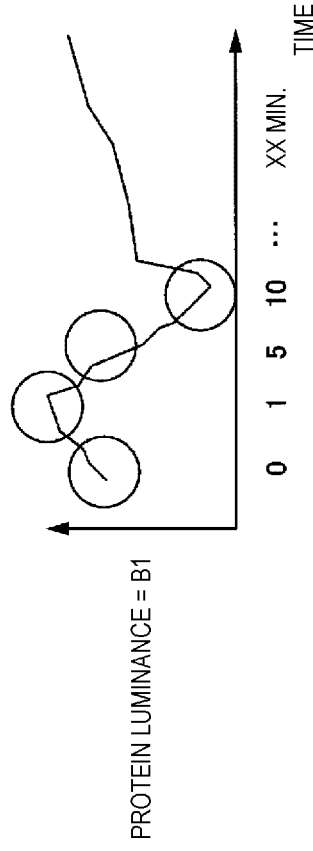

TEST WHETHER THERE IS CHANGE IN B

PROTEIN LUMINANCE = B1

FIG. 9B

CHECK WHETHER THERE IS SIGNAL: COMPARISON BETWEEN TWO GROUPS, COMPARISON BETWEEN 0 MIN. AND OTHERS

| Item | pValue_1 | EffectSize_1 | WITH CHANGE_1 | pValue_5 | EffectSize_5 | WITH CHANGE_5 | ... | pValue_XX | EffectSize_XX | WITH CHANGE_XX | Signal |
|---|---|---|---|---|---|---|---|---|---|---|---|
| B1 | 0.002 | 0.012 | × | 0.002 | 0.012 | × | ... | 0.002 | 0.012 | × | WITHOUT SIGNAL |
| B2 | 0.102 | 0.030 | × | 0.008 | 0.265 | ○ | ... | 0.005 | 0.109 | × | WITH SIGNAL |
| B3 | 0.006 | 0.456 | ○ | 0.002 | 0.327 | ○ | ... | 0.012 | 0.025 | × | WITH SIGNAL |

FIG. 11A
FOCUSED PROTEIN "A"
| NO INHIBITION | | WITH INHIBITION | | CONCLUSION OF RESULT |
|---|---|---|---|---|
| B SIGNAL | RESULT | B SIGNAL | RESULT | CONCLUSION |
| YES | WITH RESPONSE | YES | WITH RESPONSE UNDER INHIBITION | |
| | | NO | ACTIVATION | ACTIVATION |
| NO | WITHOUT RESPONSE | YES | SUPPRESSION | SUPPRESSION |
| | | NO | NO RESPONSE | NO RESPONSE |
TB1  TBR
FIG. 11B
FIG. 11C
FIG. 11D
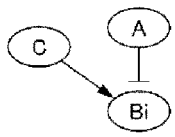

FIG. 12

| FOCUSED PROTEIN "A" | | | | | | | |
|---|---|---|---|---|---|---|---|
| COMPARISON BETWEEN NO AND WITH INHIBITION | | | | | NO INHIBITION | | CONCLUSION OF RESULT |
| B-B CORRELATION | RESULT | B-B SIGNIFICANT DIFFERENCE | RESULT | DIFFERENCE BETWEEN B-B | RESULT | A-B CORRELATION | RESULT | CONCLUSION |
| POSITIVE | SAME B-B RESPONSE | YES | DOWNSTREAM | B1 > B2 | ODDLY ACTIVATED | HIGH | DIRECT | ODDLY AND DIRECTLY ACTIVATED |
| | | | | | | LOW | INDIRECT | ODDLY AND INDIRECTLY ACTIVATED |
| | | | B2 > B1 | ODDLY SUPPRESSED | HIGH | DIRECT | ODDLY AND DIRECTLY SUPPRESSED |
| | | | | | LOW | INDIRECT | ODDLY AND INDIRECTLY SUPPRESSED |
| | | NO | NON-DOWNSTREAM | | | HIGH | HIGH POSSIBILITY OF BEING UPSTREAM | HIGH POSSIBILITY OF BEING UPSTREAM |
| | | | | | | LOW | NOT DOWNSTREAM | NOT DOWNSTREAM |
| NEGATIVE | OPPOSITE B-B RESPONSE | | | B1 > B2 | REVERSE ACTIVATION | HIGH | DIRECT | DIRECT REVERSE ACTIVATION |
| | | | | | | LOW | INDIRECT | INDIRECT REVERSE ACTIVATION |
| | | | | B2 > B1 | REVERSE SUPPRESSION | HIGH | DIRECT | DIRECT REVERSE SUPPRESSION |
| | | | | | | LOW | INDIRECT | INDIRECT REVERSE SUPPRESSION |
| NO | DIFFERENT B-B RESPONSE | | | | | | | ADJUSTMENT |
| TB2 | | TB3 | | TB4 | | TB5 | | TBR |

DIRECT

INDIRECT

DIRECT            INDIRECT

DIRECT

INDIRECT

| Comparison between no and with inhibition B-B correlation | Result | No inhibition Early period B signal | With inhibition Early period B signal | Result of early period | No inhibition Middle period B signal | With inhibition Middle period B signal | Result of middle period | No inhibition Later period B signal | With inhibition Later period B signal | Result of later period | Conclusion of result |
|---|---|---|---|---|---|---|---|---|---|---|---|
| POSITIVE | | | | | | | | | | | |
| NEGATIVE | | | | | | | | | | | |
| NOTHING | DIFFERENT B-B RESPONSE | NOTHING, NOTHING | | NO RESPONSE | NOTHING, NOTHING | | NO RESPONSE | NOTHING, NOTHING | | NO RESPONSE | NO RESPONSE |
| | | NOTHING, POSITIVE | | COMPENSATION SUPPRESSION | NOTHING, POSITIVE | | COMPENSATION SUPPRESSION | NOTHING, POSITIVE | | COMPENSATION SUPPRESSION | COMPENSATION SUPPRESSION |
| | | NOTHING, NEGATIVE | | COMPENSATION ACTIVATION | NOTHING, NEGATIVE | | COMPENSATION ACTIVATION | NOTHING, NEGATIVE | | COMPENSATION ACTIVATION | COMPENSATION ACTIVATION |
| | | POSITIVE, POSITIVE | | NOT INFLUENCED | POSITIVE, POSITIVE | | NOT INFLUENCED | POSITIVE, POSITIVE | | NOT INFLUENCED | NOT INFLUENCED |
| | | POSITIVE, NOTHING | | ACTIVATION | POSITIVE, NOTHING | | ACTIVATION | POSITIVE, NOTHING | | ACTIVATION | ACTIVATION |
| | | POSITIVE, NEGATIVE | | REVERSE ACTIVATION | POSITIVE, NEGATIVE | | REVERSE ACTIVATION | POSITIVE, NEGATIVE | | REVERSE ACTIVATION | REVERSE ACTIVATION |
| | | NEGATIVE, NEGATIVE | | NOT INFLUENCED | NEGATIVE, NEGATIVE | | NOT INFLUENCED | NEGATIVE, NEGATIVE | | NOT INFLUENCED | NOT INFLUENCED |
| | | NEGATIVE, POSITIVE | | REVERSE SUPPRESSION | NEGATIVE, POSITIVE | | REVERSE SUPPRESSION | NEGATIVE, POSITIVE | | REVERSE SUPPRESSION | REVERSE SUPPRESSION |
| | | NEGATIVE, NOTHING | | SUPPRESSION | NEGATIVE, NOTHING | | SUPPRESSION | NEGATIVE, NOTHING | | SUPPRESSION | SUPPRESSION |

TB2     TBR

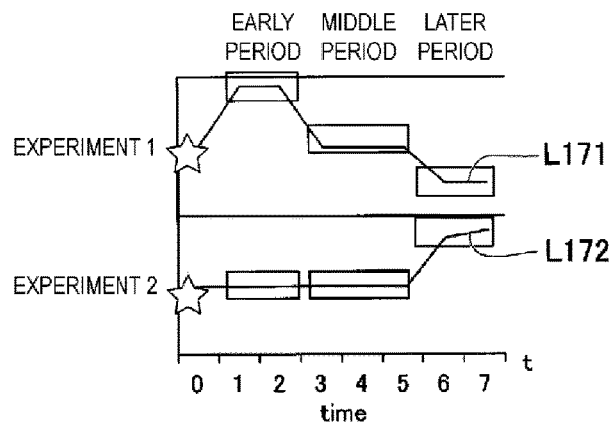

FIG. 17

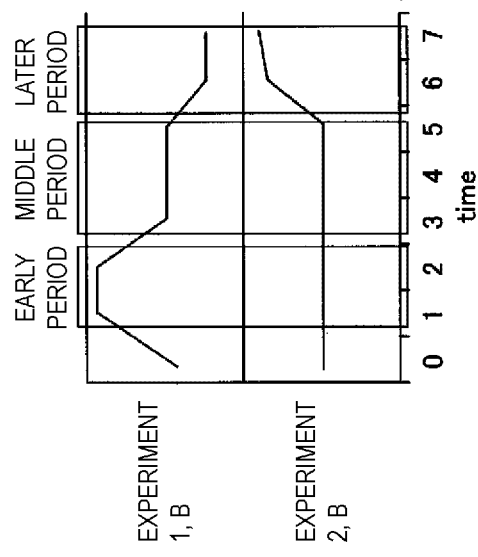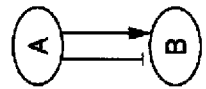
FIG. 21

ANALYSIS DEVICE, ANALYSIS PROGRAM, AND ANALYSIS METHOD

TECHNICAL FIELD

The present invention relates to an analysis device, an analysis program, and an analysis method.

BACKGROUND ART

In biological science, medical science and the like, it is known that there is a correlation between a state of an organism such as health and a disease and, for example, a state of cell(s), organelles in the cell(s) and the like. Thus, analyzing the correlation between these is one technique for solving various issues in biological science, medical science and the like. In addition, for example, analyzing signaling pathways of information transmitted between cells or within cell(s) can be helpful for research relating to biosensors in industrial applications, pharmaceutical manufacturing with the aim of preventing a disease, and the like. In various analysis techniques relating to cell(s) and tissue slices, for example, techniques using image processing are known (see Patent Document 1, for example). Traditionally, it has been desirable to analyze the relationships described above in more detail.

CITATION LIST

Patent Literature

Patent Document 1: U.S. Pat. No. 9,280,698

SUMMARY OF INVENTION

According to a first aspect of the invention, an analysis device configured to analyze an attribute of a correlation between responses with respect to a stimulus to a first subcellular component that is a subcellular component of a cell and a second subcellular component different from the first subcellular component includes an attribute analysis unit that analyzes the attribute of the correlation between the first subcellular component and the second subcellular component based on a first change in a feature value of the second subcellular component with respect to the stimulus in a state a function of the first subcellular component is suppressed and a second change in a feature value of the second subcellular component with respect to the stimulus in a state the function of the first subcellular component is not suppressed.

According to a second aspect of the invention, an analysis method for analyzing an attribute of a correlation between responses with respect to a stimulus to a first subcellular component that is a subcellular component of a cell and a second subcellular component different from the first subcellular component includes an attribute analysis step of analyzing the attribute of the correlation between the first subcellular component and the second subcellular component based on a first change in a feature value of the second subcellular component with respect to the stimulus in a state a function of the first subcellular component is suppressed and a second change in a feature value of the second subcellular component to the stimulus in a state the function of the first subcellular component is not suppressed.

According to a third aspect of the invention, an analysis program is for causing a computer, provided in an analysis device configured to analyze an attribute of a correlation between responses with respect to a stimulus to a first subcellular component that is a subcellular component of a cell and a second subcellular component different from the first subcellular component, to execute an attribute analysis step of analyzing the attribute of the correlation between the first subcellular component and the second subcellular component based on a first change in a feature value of the second subcellular component with respect to the stimulus in a state a function of the first subcellular component is suppressed and a second change in a feature value of the second subcellular component with respect to the stimulus in a state the function of the first subcellular component is not suppressed.

BRIEF DESCRIPTION OF DRAWINGS

FIG. 4 is a table showing a list of analytical results of the analysis device.

FIGS. 9A to 9B are a diagram illustrating an example of comparison between two groups and a signal determination result of comparison among multiple groups.

FIGS. 11A to 11D are a diagram illustrating an example of a network based on a result determined by a signal determining unit.

FIG. 12 is a diagram illustrating an example of a table of determination results of a correlation calculating unit, a significant difference determining unit, and a difference calculating unit.

FIG. 17 is a diagram illustrating details of analysis of "adjustment" using the difference calculating unit.

FIG. 21 is a diagram illustrating an example of a network between a subcellular component A and a subcellular component B based on a result determined by the significant difference determining unit.

DESCRIPTION OF EMBODIMENTS

Embodiment

Figure 1:
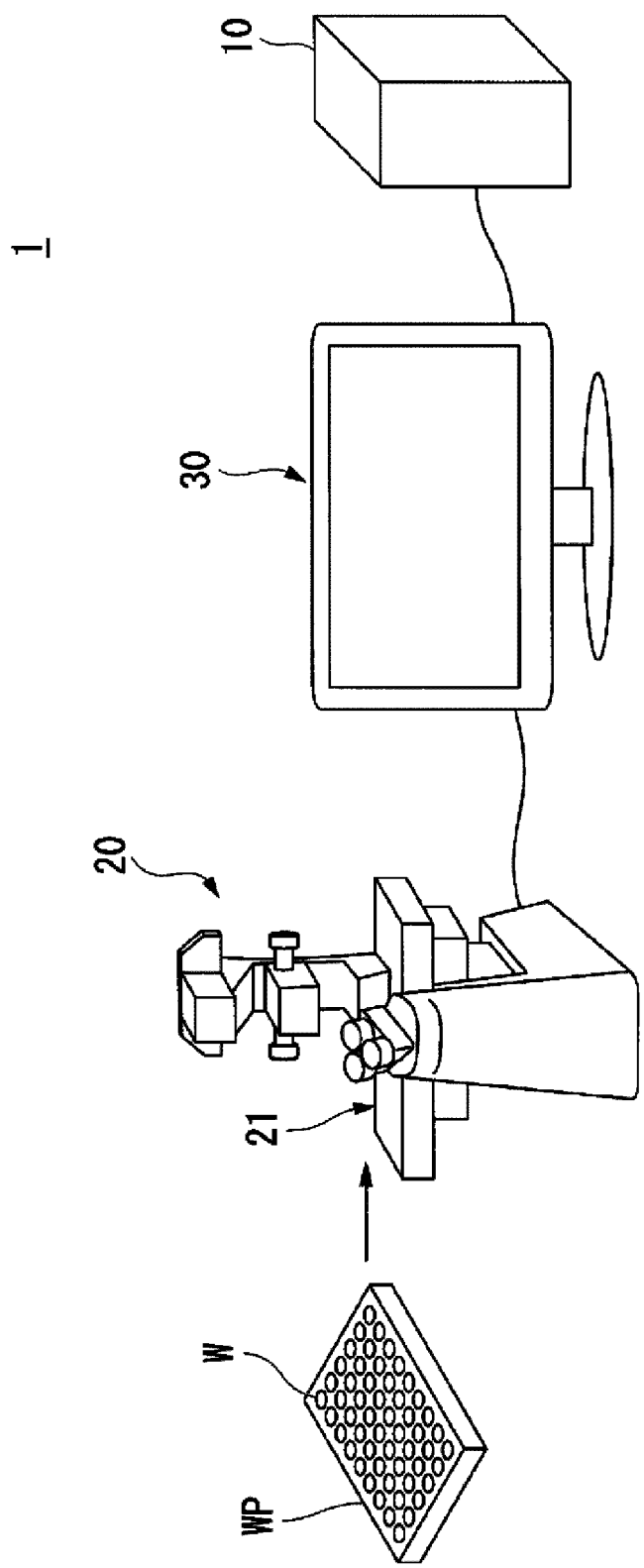
FIG. 1 is a view illustrating a configuration example of a microscope observation system according to an embodiment of the present invention.

An embodiment according to the present invention will be described below with reference to the drawings. FIG. 1 is a view illustrating a configuration example of a microscope observation system 1 according to an embodiment of the present invention.

The microscope observation system 1 performs image processing on an image acquired by capturing an image of a cell or the like. In the following description, an image acquired by capturing an image of a cell or the like is also simply referred to as a cell image.

The microscope observation system 1 includes an analysis device 10, a microscope apparatus 20, and a display 30.

The microscope apparatus 20 is a biological microscope and includes an electromotive stage 21 and an image acquiring unit 22. The electromotive stage 21 can arbitrarily move a position of an imaging target in a predetermined direction (e.g., in a certain direction within a two-dimensional plane in a horizontal direction or in a vertical direction or an axial rotation direction).

The image acquiring unit 22 includes an imaging element such as a charge-coupled device (CCD) and a complementary metal-oxide semiconductor (CMOS) and is configured to perform image capture of the imaging target on the electromotive stage 21. Note that the microscope apparatus 20 may not include the electromotive stage 21 and the stage may be a stage that does not move in a predetermined direction.

More specifically, the microscope apparatus 20 has, for example, functions such as a differential interference contrast microscope (DIC), a phase difference microscope, a fluorescence microscope, a confocal microscope, a super-resolution microscope, a two-photon excitation fluorescence microscope, a light sheet microscope, a light field microscope, a holographic microscope, and optical coherence tomography (OCT).

The microscope apparatus 20 performs image capture of a culture vessel placed on the electromotive stage 21. The culture vessel is, for example, a well plate WP, a slide chamber, or the like. The microscope apparatus 20 irradiates cell(s) cultured in a plurality of wells W provided in the well plate WP with light, and thus performs image capture of transmitted light that the cell(s) have transmitted, as an image of the cell(s). In this way, the microscope apparatus 20 can acquire an image of the cell(s) such as a transmission DIC image, a phase contrast image, a dark field image, and a bright field image.

Further, the cell(s) is irradiated with excitation light exciting a fluorescent material, and thus the microscope apparatus 20 performs image capture of fluorescence emitted from a biological material, as an image of the cells. Furthermore, the microscope apparatus 20 performs image capture of light emission or phosphorescence from a fluorescent material in a cell, as an image of the cell(s).

In the embodiment, cell(s) is stained alive and a time-lapse image captured to acquire an image of a change in the cell(s) obtained after cell stimulation. In the embodiment, a fluorescent fusion protein is expressed, or cell(s) is stained alive with a chemical reagent or the like to acquire a cell image. In yet another embodiment, cell(s) is fixed and stained to acquire a cell image. The fixed cell(s) stops metabolism. Accordingly, in a case where cell(s) is stimulated and subsequently a time-dependent intracellular change is observed with fixed cell(s), a plurality of cell culture vessels seeded with cell(s) is required to be prepared. For example, there is a case in which cell(s) is stimulated, and it is desired to observe a change in the cell(s) after a lapse of a first duration of time and a change in the cell(s) after a lapse of a second duration of time being different from the first duration of time. In this case, cell(s) is stimulated, and after a lapse of the first duration of time, the cell(s) is fixed and stained to acquire a cell image.

On the other hand, a cell culture vessel seeded with cell(s) different from the cell(s) used for the observation in the first duration of time is prepared. The cell(s) is stimulated and after a lapse of the second duration of time, the cell(s) is fixed and stained to acquire a cell image. In this way, a change in a cell during the first duration of time and a change in a cell during the second duration of time are observed, and thus a time-dependent intracellular change can be estimated. In addition, the number of cells used to observe the intracellular changes during the first duration of time and the second duration of time is not limited to one. Accordingly, a plurality of cell images are to be acquired during each of the first duration of time and the second duration of time. For example, in a case where the number of cells used to observe an intracellular change is 1000, 2000 cells are to be performed image capture during the first and second durations of time. Accordingly, in the case of attempting to acquire details of an intracellular change due to a stimulus, a plurality of cell images are required for each of the timings of image capturing from when the stimulus is applied, and thus a large amount of cell images are acquired.

In addition, the microscope apparatus 20 may perform image capture, as the above-described cell images, of luminescence or fluorescence emitted from a chromogenic material itself incorporated in a biological material or of luminescence or fluorescence emitted from a material having a chromophore and combined with a biological material. In this way, the microscope observation system 1 can acquire a fluorescence image, a confocal image, a super-resolution image, and a two-photon excitation fluorescence microscopy image.

Note that a method for acquiring an image of cell(s) is not limited to using an optical microscope. For example, the method for acquiring an image of cell(s) may be using an electron microscopy. In addition, as for the image of cell(s), a correlation may be acquired by using an image acquired by a different scheme. That is, a type of an image of cell(s) may be selected appropriately.

The cell(s) in the embodiment are, for example, primary cultured cell(s), established cultured cell(s) strains, and cell(s) in a tissue section. To observe the cell(s), samples to be observed may be aggregations of cell(s) or tissue samples, organs, or individuals (for example, animals), and an image including cell(s) may be acquired. Note that a state of cell(s) is not particularly limited to a specific state, and the cell(s) may be in a living state or may be in a fixed state. The state of cell(s) may be "in-vitro". As a matter of course, information about the living state may be combined with information about the fixed state.

In addition, cell(s) may be treated with chemiluminescent or fluorescent proteins (for example, chemiluminescent or fluorescent proteins expressed from introduced genes (such as green fluorescent proteins (GFP)) to be observed. Alternatively, cell(s) may be observed by using staining such as immunostaining or staining with chemical reagents. The observation may be conducted by using a combination of the above-described treatment and staining. For example, a luminescent protein to be used can be selected in accordance with a determination type of an intranuclear structure (for example, Golgi body or the like) in a cell.

In addition, the pretreatment for analyzing correlation acquisition such as means for observing cell(s); and a method for staining cell(s) may be selected appropriately in accordance with the purpose. For example, dynamic information about cell(s) may be acquired by a technique optimal for the case of acquiring a dynamic behavior of cell(s), and information about intracellular signaling pathway may be acquired by a technique optimal for the case of acquiring intracellular signaling pathway. The pretreatment selected in accordance with the purpose may be different.

The well plate WP includes one or more wells W. In the embodiment, the well plate WP includes 96 (8×12) wells W as illustrated in FIG. 1. The number of wells provided in the well plate WP is not limited thereto and may have 48 (6×8) wells W, 24 (6×4) wells W, 12 (3×4) wells W, 6 (2×3) wells W, 384 (12×32) wells W, or 1536 (32×48) wells W. Cell(s) is cultured in the wells W under specific experimental conditions. The specific experimental conditions include temperature, humidity, a culturing period, an elapsed time period from when a stimulus is applied, a type and strength of an applied stimulus, concentration, an amount, presence or absence of a stimulus, induction of biological characteristics, and the like. The stimulus is, for example, a physical stimulus such as electricity, sound waves, magnetism, and light; or a chemical stimulus acquired by administering a substance or a medication. In addition, the biological characteristics are characteristics indicating a stage of cell differentiation, morphology, the number of cells, an intracellular behavior of molecules, morphology and a behavior of organelles, each of the forms, a behavior of an intranuclear structure, a behavior of DNA molecules, and the like.

Subcellular Component of Cell

Figure 2:
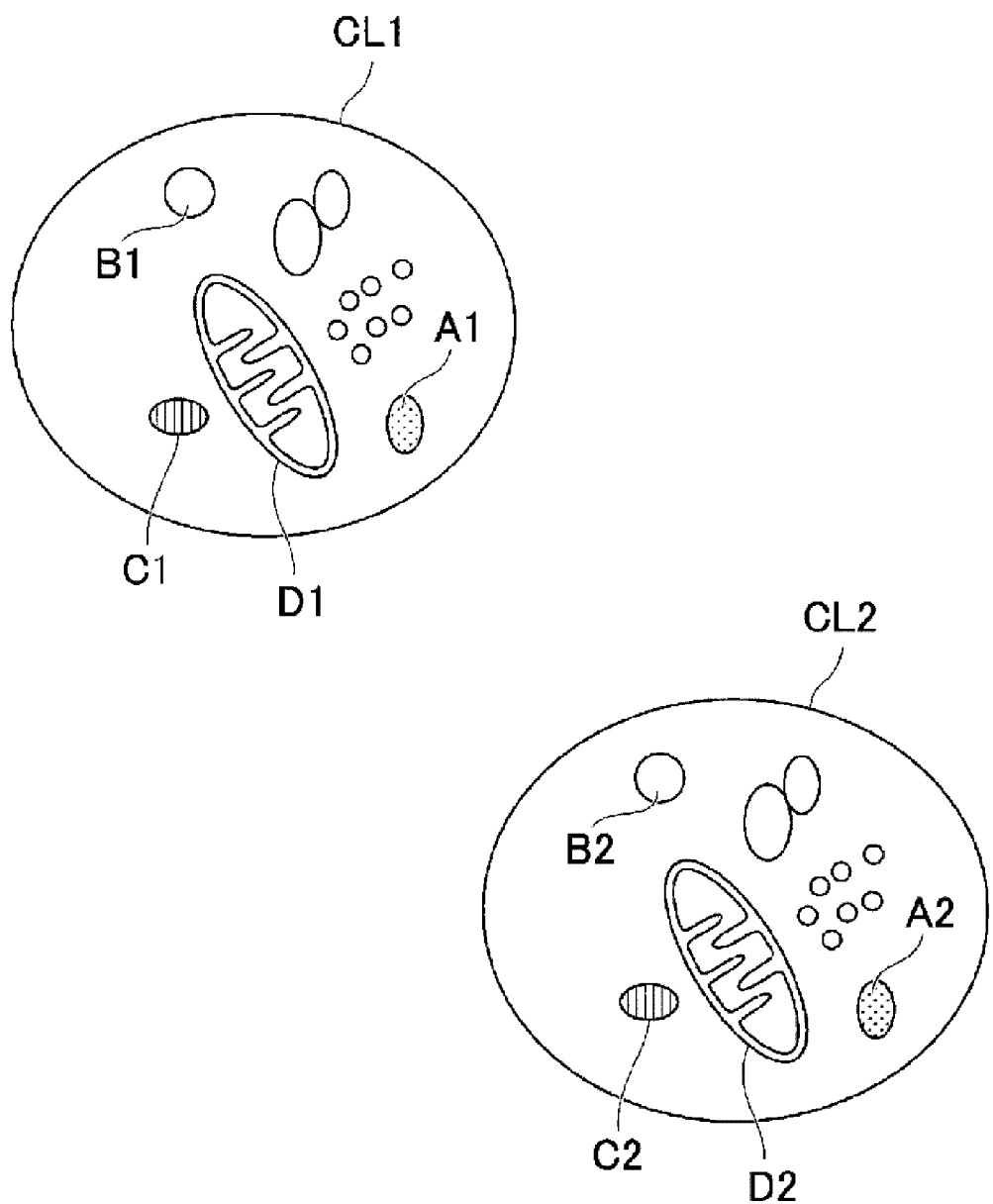
FIG. 2 is a view illustrating examples of cells CL.

Referring now to FIG. 2, subcellular components of a cell will be described. The subcellular components of the cell include various types of protein constituting the cell.

FIG. 2 is a view illustrating examples of cells CL.

FIG. 2 illustrates a cell CL1 and a cell CL2 that are each the same type of cell. The same type of stimulus is applied to the cells CL1 and CL2.

The same type of stimulus is applied to the cells CL1 and CL2.

In the present embodiment, subcellular components of the cell CL1 include a subcellular component A1, a subcellular component B1, a subcellular component C1, and a subcellular component D1. Subcellular components of the cell CL2 include a subcellular component A2, a subcellular component B2, a subcellular component C2, and a subcellular component D2. The subcellular component A1 and the subcellular component A2, the subcellular component B1 and the subcellular component B2, the subcellular component C1 and the subcellular component C2, and the subcellular component D1 and the subcellular component D2, are individually the same type of subcellular component.

In the following description, when the cell CL1 and the cell CL2 are not distinguished from each other, they are also simply referred to as the cells CL. When the subcellular component A1 and the subcellular component A2 are not distinguished from each other, they are also simply referred to as subcellular components A. Likewise, when the subcellular component B1 and the subcellular component B2 are not distinguished from each other, they are also simply referred to as subcellular components B. When the subcellular component C1 and the subcellular component C2 are not distinguished from each other, they are also simply referred to as subcellular components C. When the subcellular component D1 and the subcellular component D2 are not distinguished from each other, they are also simply referred to as subcellular components D.

The subcellular component A, the subcellular component B, the subcellular component C, and the subcellular component D are different from each other.

The analysis device 10 analyzes an attribute of a correlation between responses of the subcellular component A1 and the subcellular component B1, being each a subcellular component of the cell CL, to a stimulus.

Correlation

Here, a correlation to be analyzed by the analysis device 10 will be described. For example, a stimulus is applied to the cell CL1. When the subcellular component A1 and the subcellular component B1 in the cell CL1 subjected to the stimulus exhibit a correlated response to the stimulus, there is a correlation between the subcellular component A1 and the subcellular component B1. The correlation between the subcellular components is illustrated as a network. In the following description, subcellular components included in the network are also referred to as nodes. The network includes the nodes, edges, and the like. The network is represented by the nodes and the edges connecting the respective nodes. The network indicates that there is a correlation between the nodes connected by the corresponding edges. The network also indicates that there is no correlation between the nodes that are not connected by the respective edges. In this example, a node A1 indicating the subcellular component A1 described above and a node B1 indicating the subcellular component B1 have a correlation, so they are connected by an edge.

Here, the correlation refers to a relationship in which fluctuation, maintenance, elimination, and expression of a certain subcellular component influence fluctuation, maintenance, elimination, and expression of another subcellular component or refers to a relationship in which fluctuation, maintenance, elimination, and expression of a certain subcellular component influence the fluctuation, maintenance, elimination, and expression of the subcellular component itself. Note that these relationships are unidirectional, bidirectional or feedback relationships.

Attributes of Correlation

Next, an attribute of the correlation will be described. The attribute of the correlation indicates a mutual attribute of the correlation. The mutual attribute is a relation in the correlation. The relations in the correlation include presence or absence of an edge indicating whether there is a correlation, directionality of an edge indicating a causal relationship of a correlation, a shape of an edge indicating a relationship between subcellular components for suppression or activation, and the like, for example.

Here, the relationship between the subcellular components for suppression refers to a relationship in which the subcellular component B1 is activated by suppressing a function of the subcellular component A1. In this case, the subcellular component A1 suppresses the subcellular component B1. Suppressing a function of a subcellular component includes functional suppression of the subcellular component, displacement or deletion thereof, and a low expression state of the subcellular component or no expression state thereof. For example, when a function of a subcellular component is defined as an expression level of the subcellular component, the expression level may be reduced by 10% by suppressing the function of the subcellular component or may decrease by 20%, 30%, 40%, 50%, 60%, 70%, 80%, 90%, or 100%. In the following description, suppressing a function of a subcellular component function using an inhibitor or the like is also referred to as inhibiting a function of a subcellular component.

The relationship between the subcellular components for activation refers to a relationship in which activation of the subcellular component B1 is lost by suppressing the function of the subcellular component A1, for example. In this case, the subcellular component A1 activates the subcellular component B1.

The attribute of the correlation also includes not only a correlation between nodes, but also an attribute of a correlation caused by another subcellular component. For example, a case in which a certain subcellular component C1 has a function of suppressing the subcellular component B1 will be described. This subcellular component C1 is activated by the subcellular component A1. When activation of the function of the subcellular component A1 is lost, the subcellular component C1 is suppressed. The subcellular component C1 suppressed stops a function of suppressing the subcellular component B1. This activates the subcellular component B1.

When activation of the subcellular component A1 is lost by suppressing the subcellular component A1, the subcellular component C1 is suppressed and the subcellular component B1 is activated. This case also can be said that there is a correlation between the subcellular component A1 and the subcellular component B1. That is, an attribute of the correlation is a state of activation of the subcellular component A and the subcellular component B due to a stimulus.

The attribute of the correlation can also be said that the subcellular component A1 is positioned upstream of a relationship with the subcellular component B1. Likewise, the subcellular component A1 is positioned upstream of a relationship with the subcellular component C1. The subcellular component C1 is positioned upstream of a relationship with the subcellular component B1. That is, the attribute of the correlation is the order of activation or inhibition of the subcellular component A and the subcellular component B due to a stimulus.

While the subcellular component B1 and the subcellular component A1 do not have a direct correlation, they have a correlation via the subcellular component C1. There is a correlation associated with the order of description of the subcellular component A1, the subcellular component C1, and the subcellular component B1. The analysis device 10 analyzes an attribute of the correlations as described above.

Analysis of Attributes of Correlation

Here, experiments to be analyzed by the analysis device 10 will be described. In this example, the cell CL1 and the cell CL2 illustrated in FIG. 2 described above are each cultured in a different well plate. As described above, the cell CL1 and the cell CL2 are each the same type of cell and are each subjected to the same type of stimulus. Then, the cell CL1 and the cell CL2 may be cultured in the same well plate. In this case, when a chemical solution is used as a stimulus, for example, the chemical solution may be dropped onto cultured cells containing the cell CL1 and the cell CL2 to apply the stimulus to each of the cell CL1 and the cell CL2.

In a well plate in which the cell CL1 is cultured, the function of the subcellular component A1 is not suppressed. To a well plate in which the cell CL2 is cultured, an inhibitor composed of a compound is applied to suppress the subcellular component A1. Thus, the well plate in which the cell CL1 is cultured and the well plate in which the cell CL2 is cultured are different from each other in that whether the inhibitor for suppressing the function of the subcellular component A1 is applied thereto. The well plate in which the cell CL1 is cultured and the well plate in which the cell CL2 is cultured are different from each other in that whether processing for suppressing a function is applied to the subcellular component A1. The inhibitor is not limited to a compound and may be an enzyme. In addition, genetic modification, gene editing, or the like, may cause functional inhibition of a subcellular component, mutation or deletion thereof, or a low expression state of the subcellular component or no expression state thereof. Thus, the inhibitor may be applied to a subcellular component, or the subcellular component may be altered by genetic modification or gene editing.

The analysis device 10 analyzes an attribute of a correlation by comparing experimental results acquired from experiments without suppressing the subcellular component A1 with experimental results acquired from experiments with suppressing the subcellular component A2.

In the present embodiment, an experiment with the subcellular component A2 suppressed inhibits a function of the subcellular component A2 and loses activity of the function of the subcellular component A2, so results of the experiment are referred to as inhibited experimental results. In addition, a cell with the subcellular component A2 inhibited is also referred to as an inhibited cell. Experimental results acquired from experiments without inhibiting the subcellular component A1 are also referred to as controlled experimental results. A cell with the subcellular component A1 that is not inhibited is also referred to as a controlled cell. That is, the controlled experimental results are changes in the cell CL1 with elapse of time.

The analysis device 10 of the present embodiment includes an analysis unit that compares a feature value obtained from an image acquired by capturing an inhibited experimental result to a feature value obtained from an image acquired by capturing a controlled experimental result. For example, when this feature value is luminance of the subcellular component B, luminance of the subcellular component B2 acquired by capturing an inhibited experimental result is compared to luminance of the subcellular component B1 acquired by capturing a controlled experimental result. In this way, the analysis device 10 analyzes an attribute of a correlation between the subcellular component A and the subcellular component B. In the following description, comparison between a feature value of the subcellular component B2 acquired from an inhibited experimental result and a feature value of the subcellular component B1 acquired from a controlled experimental result is also referred to as comparison between B-B.

That is, the analysis unit analyzes an attribute of the correlation between the subcellular component A and the subcellular component B based on change in a feature value of the subcellular component B to a stimulus when the subcellular component A is suppressed and change in a feature value of the subcellular component B to a stimulus when the subcellular component A is not suppressed.

Specifically, the analysis unit analyzes the attribute of the correlation between the subcellular component A and the subcellular component B based on at least one of six analytical results described below. The six analyses include: (1) an analysis of whether there is a signal of the subcellular component B of a controlled experimental result; (2) an analysis of whether there is a signal of the subcellular component B based on a controlled experimental result and an inhibited experimental result; (3) an analysis of whether feature values between B-B change at the same timing; (4) an analysis of whether variations in the feature values between B-B are different from each other; (5) an analysis of the variations in the feature values between B-B; and (6) analysis of a controlled experimental result based on the correlation between the subcellular component A and the subcellular component B. Methods of the six analyses will be described below in detail.

Functional Constitution of Analysis Device 10

Figure 3:
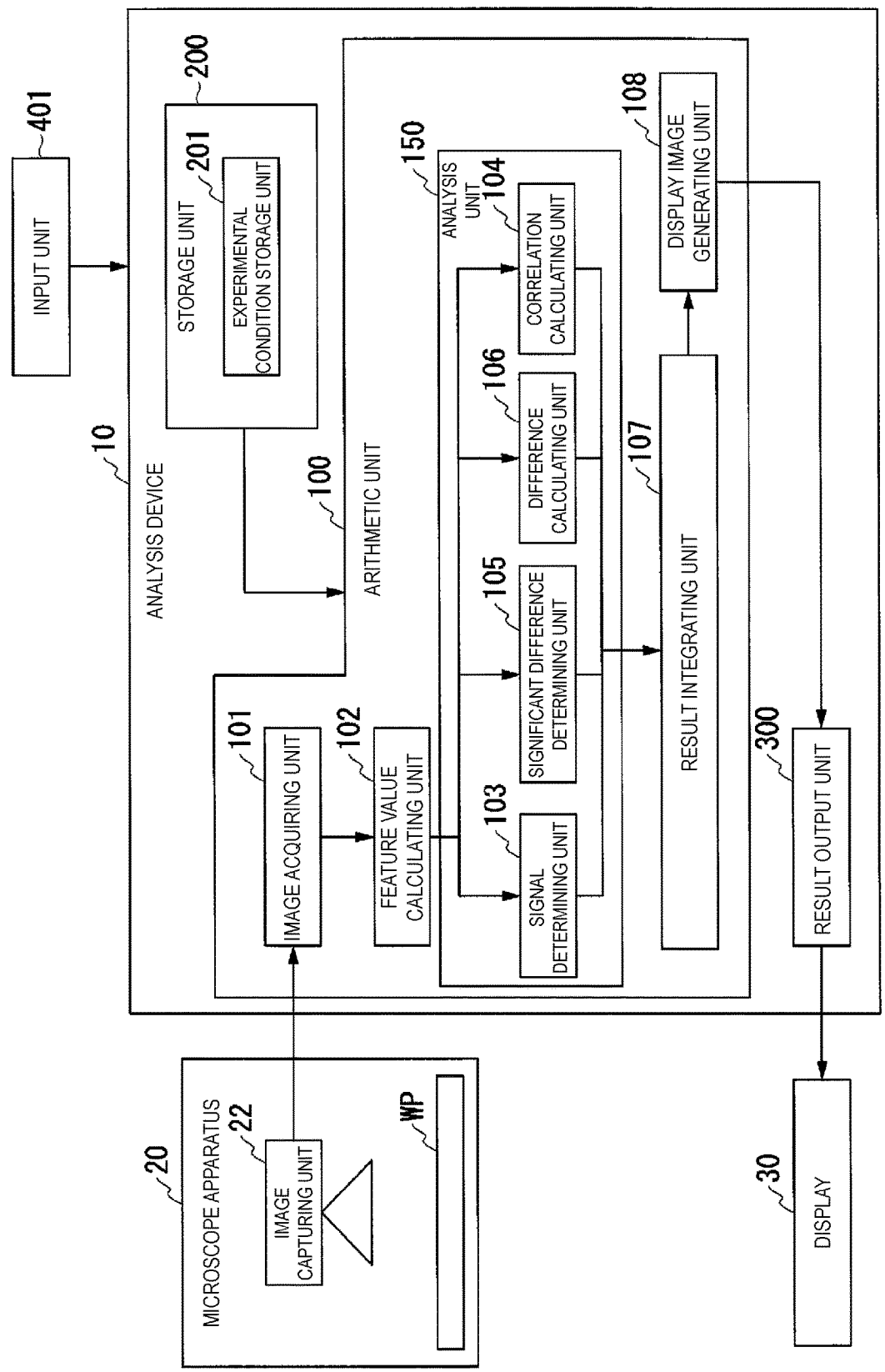
FIG. 3 is a block diagram illustrating an example of a functional configuration of each of the units provided in an analysis device according to the present embodiment.

FIG. 3 is a block diagram illustrating an example of a functional configuration of each of the units provided in the analysis device 10 according to the present embodiment. In the present embodiment, the analysis device 10 analyzes an attribute of a correlation between responses of a first subcellular component of the cell CL and a second subcellular component of the cell CL2 with respect to a stimulus by analyzing an image acquired by capturing an image of a cell subjected to the stimulus using the microscope apparatus 20. In the following description, the first subcellular component is referred to as a subcellular component A. In the following description, the second subcellular component is referred to as a subcellular component B. The first subcellular component and the second subcellular component are not limited to the subcellular component A and the subcellular component B, respectively, and any combination of subcellular components may be used as long as the subcellular components are different from each other and are combined with each other.

The analysis device 10 includes an arithmetic unit 100, a storage unit 200, and a result output unit 300.

The arithmetic unit 100 functions by allowing a processor to execute a program stored in the storage unit 200. In addition, some or all of these functional units of the arithmetic unit 100 may include hardware such as a large scale integration (LSI) or an application specific integrated circuit (ASIC). In addition to an analysis unit 150 described above, the arithmetic unit 100 includes a cell image acquiring unit 101, a feature value calculating unit 102, a result integrating unit 107, and a display image generating unit 108.

The cell image acquiring unit 101 acquires cell images captured by the image acquiring unit 22 and feeds the cell images acquired to the feature value calculating unit 102. Here, the cell images acquired by the cell image acquiring unit 101 include a plurality of images acquired by capturing images of cell culture states in time series. The cell images each are acquired by capturing images of the inhibited cell and the controlled cell described above.

The feature value calculating unit 102 acquires the cell images from the cell image acquiring unit 101. The feature value calculating unit 102 calculates feature values of subcellular components constituting cell(s) captured in the cell images acquired from the cell image acquiring unit 101. The feature values include brightness of the cell images, cell area of the images, distribution of the brightness of the cell images within the image, a shape and the like. That is, the feature values include a characteristic derived from information acquired from the captured cell images. That is, the feature values include a characteristic derived from information acquired from the captured cell images. For example, the distribution of the brightness in the acquired images is calculated. The feature value calculating unit 102 may acquire positional information indicating change in luminance different from another, from change in calculated luminance distribution during a predetermined time or from change in the calculated luminance distribution with change in a cellular state such as differentiation, using a plurality of images in time series or images different in change in the cellular state such as differentiation, to define the change in luminance as a feature value.

In addition, the feature value calculating unit 102 may be configured to extract dynamic feature values, by observing each of the plurality of images captured at a predetermined time interval, such as cell contraction, a heartbeat cycle, a cell migration rate, a change in degree of nuclear chromatin aggregation being an indicator of healthy and dying cells that are less affected by stimulus, a change rate in the number and lengths of processes of neurons, the number of synapses in neurons, neural activity such as a membrane potential change, a change in intracellular calcium concentration, second messenger activity, a morphological change of an organelle, an intracellular behavior of molecules, a nuclear morphology, a behavior of an intranuclear structure, and a behavior of DNA molecules. These feature values extraction methods use, for example, Fourier transformation, Wavelet transformation, and temporal differentiation and use a moving average for noise removal.

The feature value calculating unit 102 calculates feature values based on cell images acquired by capturing images of the inhibited cell(s) described above and cell images acquired by capturing images of the controlled cell. In the following description, a feature value calculated from cell images acquired by capturing images of an inhibited cell is also referred to as an inhibited feature value. Thus, the inhibited feature value includes a feature value of a subcellular component constituting the inhibited cell, the feature value being calculated from the cell images acquired by capturing images of the inhibited cell. When there is provided a plurality of feature values of the subcellular component constituting the inhibited cell, the plurality of feature values being calculated from the cell images acquired by capturing images of the inhibited cell, the inhibited feature value includes the plurality of feature values. In addition, a feature value calculated from cell images acquired by capturing images of a controlled cell is also referred to as a controlled feature value. Thus, the controlled feature value includes a feature value of a subcellular component constituting the controlled cell, the feature value being calculated from the cell images acquired by capturing images of the controlled cell. When there is provided a plurality of feature values of the subcellular component constituting the controlled cell, the plurality of feature values being calculated from the cell images acquired by capturing images of the controlled cell, the controlled feature value includes the plurality of feature values.

Here, analytical results acquired by analysis using the analysis device 10 will be described with reference to FIG. 4.

FIG. 4 is a table showing a list of analytical results of the analysis device 10.

The analysis unit 150 includes a signal determining unit 103, a correlation calculating unit 104, a significant difference determining unit 105, and a difference calculating unit 106.

The signal determining unit 103 analyzes items of Table TB1 in FIG. 4.

The correlation calculating unit 104 analyzes items of Table TB2 and Table TB5 in FIG. 4.

The significant difference determining unit 105 analyzes items of Table TB3 in FIG. 4.

The difference calculating unit 106 analyzes items of Table TB4 in FIG. 4.

The signal determining unit 103 analyzes (1) and (2) of the six analyses described above. The signal determining unit 103 feeds analytical results to the result integrating unit 107.

Specifically, the signal determining unit 103 analyzes whether there is a signal of the subcellular component B1 based on the controlled feature value, as an analysis of (1). In a case where the controlled feature value includes a signal from the subcellular component B1, the signal determining unit 103 determines the case as "with response". In a case where the controlled feature value includes no signal from the subcellular component B1, the signal determining unit 103 determines the case as "without response".

The signal determining unit 103 determines whether there is a signal of the subcellular component B2 based on the controlled feature value and the inhibited feature value, as an analysis of (2).

Specifically, in a case where the controlled feature value includes a signal from the subcellular component B1 and where the inhibited feature value includes a signal from the subcellular component B2, the signal determining unit 103 determines the case as "with response under inhibition" as analytical results of (1). This indicates that there is a signal from the subcellular component B2 even when the subcellular component A is inhibited.

In a case where the controlled feature value includes a signal from the subcellular component B1 and where the inhibited feature value includes no signal from the subcellular component B2, the signal determining unit 103 determines the case as ""activation" as analytical results of (1). This indicates that the subcellular component A activates the subcellular component B.

In a case where the controlled feature value includes no signal from the subcellular component B1 and where the inhibited feature value includes a signal from the subcellular component B2, the signal determining unit 103 determines the case as "suppression" as analytical results of (1). This indicates that the subcellular component A suppresses the subcellular component B.

In a case where the controlled feature value includes no signal from the subcellular component B1 and where the inhibited feature value includes no signal from the subcellular component B2, the signal determining unit 103 determines the case as "no response" as analytical results of (1). This indicates that the subcellular component B is not responsive in this experimental system.

The correlation calculating unit 104 analyzes (3) and (6) of the six analyses described above. Specifically, the correlation calculating unit 104 analyzes an attribute of the correlation between the subcellular component A and the subcellular component B based on strength of a correlation between a feature value of the subcellular component A and a feature value of the subcellular component B. The correlation calculating unit 104 feeds analytical results based on calculation results for the correlation to the result integrating unit 107.

More specifically, as shown in Table TB2 of FIG. 4, the correlation calculating unit 104 calculates a correlation between the feature value of the subcellular component B2 included in the inhibited feature value and the feature value of the subcellular component B1 included in the controlled feature value, as an analysis of (3).

In a case where analytical results of (2) indicate "with response under inhibition" and where analytical results of (3) indicate that a calculated correlation is a positive correlation, the correlation calculating unit 104 determines the case as "same B-B response". This indicates that the feature value of the subcellular component B1 included in the controlled feature value and the feature value of the subcellular component B2 included in the inhibited feature value are each the same response.

In a case where analytical results of (2) indicate "with response under inhibition" and where analytical results of (3) indicate that a calculated correlation is a negative correlation, the correlation calculating unit 104 determines the case as "opposite B-B response". This indicates that the feature value of the subcellular component B1 included in the controlled feature value and the feature value of the subcellular component B2 included in the inhibited feature value are each an opposite response.

In a case where analytical results of (2) indicate "with response under inhibition" and where analytical results of (3) indicate that there is no calculated correlation, the correlation calculating unit 104 determines the case as "different B-B response". This indicates that the subcellular component B1 included in the controlled feature value and the subcellular component B2 included in the inhibited feature value each respond at a different timing.

As shown in Table TB5 of FIG. 4, the correlation calculating unit 104 calculates a correlation between the feature value of the subcellular component A1 included in the controlled feature value and the feature value of the subcellular component B1, as an analysis of (6).

The correlation calculating unit 104 calculates that there is the correlation between the feature value of the subcellular component A1 included in the controlled feature value and the feature value of the subcellular component B1 when the feature value of the subcellular component A1 included in the controlled feature value and the feature value of the subcellular component B1 each change at the same timing.

More specifically, the correlation calculating unit 104 determines that the subcellular component A "directly" suppresses or activates the subcellular component B when a correlation between the feature value of the subcellular component A1 included in the controlled feature value and the feature value of the subcellular component B1 is high, as shown in Table TB5 of FIG. 4.

In addition, the correlation calculating unit 104 determines that the subcellular component A "indirectly" suppresses or activates the subcellular component B when the correlation between the feature value of subcellular component A1 included in the controlled feature value and the feature value of the subcellular component B1 is low, as shown in Table TB5 of FIG. 4.

The correlation calculating unit 104 determines that the subcellular component B has "high possibility of being upstream" of the subcellular component A when analytical results of (4) described below are determined as "non-downstream" and the correlation between the feature value of subcellular component A1 included in the controlled feature value and the feature value of the subcellular component B1 is "high". This indicates that the subcellular component A is suppressed or activated by the subcellular component B.

In addition, the correlation calculating unit 104 determines that the subcellular component A is "not downstream" of subcellular component B when analytical results of (4) described below are determined as "non-downstream" and the correlation between the feature value of the subcellular component A1 included in the controlled feature value and the feature value of the subcellular component B1 is "low".

This indicates that subcellular component A is not influenced by inhibition or activation from the subcellular component B.

The significant difference determining unit 105 analyzes (4) of the six analyses described above. Specifically, the significant difference determining unit 105 analyzes an attribute of the correlation between the subcellular component A and the subcellular component B based on difference between the inhibited feature value and the controlled feature value. The significant difference determining unit 105 feeds analytical results to the result integrating unit 107.

Specifically, the significant difference determining unit 105 analyzes (4) whether variations in the feature values between B-B are different from each other, as shown in Table TB3 of FIG. 4.

More specifically, the significant difference determining unit 105 determines the attribute of the correlation based on difference between the inhibited feature value and the controlled feature value. The significant difference determining unit 105 determines that the subcellular component A is "downstream" of the subcellular component B when analytical results of (3) indicate "same B-B response" and analytical results of (4) indicate that there is a difference in a variation.

The significant difference determining unit 105 determines that the subcellular component A is "non-downstream" of the subcellular component B when the analytical results of (3) indicate "same B-B response" and the analytical results of (4) indicate that there is no difference in the variation. This indicates that the subcellular component A is not influenced by inhibition or activation from the subcellular component B.

The difference calculating unit 106 analyzes (5) of the six analyses described above. Specifically, the difference calculating unit 106 analyzes the attribute of the correlation between the subcellular component A and the subcellular component B based on difference between a variation of the inhibited feature value and a variation of the controlled feature value. The difference calculating unit 106 feeds analytical results to the result integrating unit 107.

Specifically, the difference calculating unit 106 analyzes (5) the variations in the feature values between B-B, as shown in Table TB4 of FIG. 4. The difference calculating unit 106 determines that the subcellular component A "oddly activates" the subcellular component B when analytical results of (4) described above indicate the "downstream" and the feature value of the subcellular component B1 is more than the feature value of the subcellular component B2.

The difference calculating unit 106 also determines that the subcellular component A "oddly suppresses" the subcellular component B when the analytical results of (4) described above indicate "downstream" and the feature value of the subcellular component B1 is less than the feature value of the subcellular component B2.

The difference calculating unit 106 determines that the subcellular component A "reversely activates" the subcellular component B when analytical results of (3) described above indicate the "opposite B-B response" and the feature value of the subcellular component B1 is more than the feature value of the subcellular component B2.

In addition, the difference calculating unit 106 determines that the subcellular component A "reversely suppresses" the subcellular component B when the analytical results of (3) described above described above indicate the "opposite B-B response" and the feature value of the subcellular component B1 is less than the feature value of the subcellular component B2.

The result integrating unit 107 acquires the analytical results from each of the signal determining unit 103, the correlation calculating unit 104, the significant difference determining unit 105, and the difference calculating unit 106. The result integrating unit 107 integrates the analytical results acquired. The result integrating unit 107 feeds the analytical results integrated to the display image generating unit 108.

The display image generating unit 108 acquires the analytical results from the result integrating unit 107. The display image generating unit 108 generates an image of a network indicating the attribute of the correlation between the subcellular component A and the subcellular component B based on the analytical results acquired from the result integrating unit 107. The display image generating unit 108 feeds the generated image of the network to the result output unit 300.

The result output unit 300 outputs calculation results calculated by the arithmetic unit 100 to the display 30. The result output unit 300 may output the calculation results calculated by the arithmetic unit 100 to an output device other than the display 30, a storage device, or the like.

The display 30 displays the calculation results calculated by the arithmetic unit 100 and output from the result output unit 300. Specifically, the display 30 displays the image of the network output from the result output unit 300 or a list of results.

Overview of Operation of Analysis Device

A specific computation procedure of the arithmetic unit 100 described above will be described with reference to FIG. 5.

Figure 5:
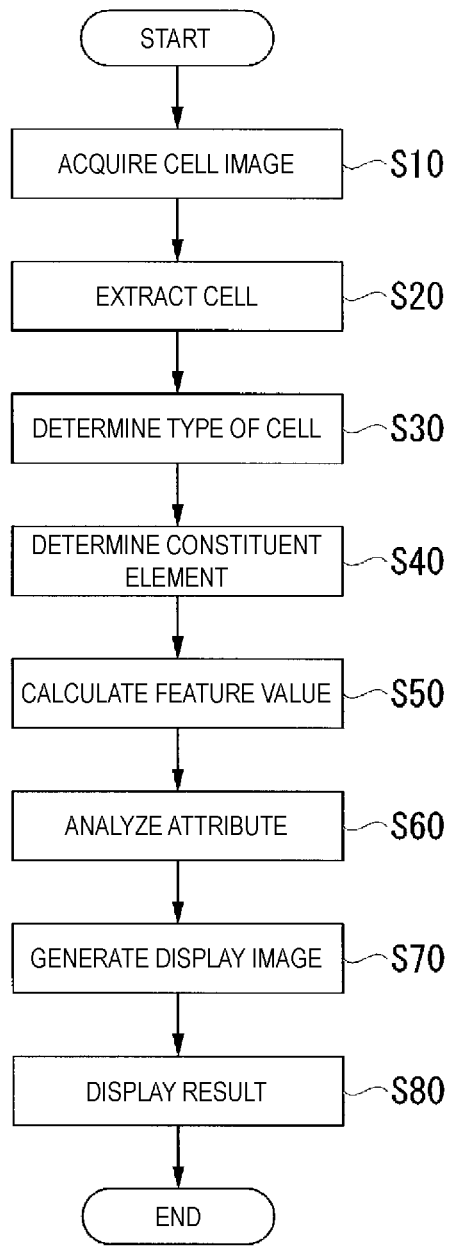
FIG. 5 is a flowchart illustrating an example of a computation procedure of an arithmetic unit according to the present embodiment.

FIG. 5 is a flowchart illustrating an example of the computation procedure of the arithmetic unit 100 according to the present embodiment. The computation procedure described here is an example, and the computation procedure may be eliminated, or another computation procedure may be added.

The cell image acquiring unit 101 acquires cell images (step S10). The cell images include images of multiple types of biological tissue different in size, such as a gene, a protein, and an organelle. The cell images also include cell shape information. The cell images include information such as a phenotype, a metabolite, a protein, and a gene, so that the analysis device 10 can analyze correlations among them.

The feature value calculating unit 102 extracts an image of a cell included in the cell images acquired in step S10 for each cell (step S20). The feature value calculating unit 102 extracts the image of a cell by applying image processing to the cell images. In this example, the feature value calculating unit 102 extracts the image of a cell by performing outline extraction, pattern matching, and the like on the cell images.

Next, the feature value calculating unit 102 determines a type of a cell for the image of the cell, extracted in step S20 (step S30). In addition, the feature value calculating unit 102 determines a subcellular component of the cell included in the image of the cell extracted in step S20 based on a determination result in step S30 (step S40). Here, subcellular components of the cell include cell organelles such as a cell nucleus, a lysosome, a Golgi body, and a mitochondrion, and a protein constituting an organelle, for example. While a type of a cell is determined in step S30, the type of a cell may not be determined. In this case, when a type of a cell to be introduced is preliminarily determined, this information may be used. As a matter of course, a type of a cell may not be identified.

Subsequently, the feature value calculating unit 102 calculates a feature value of the image as a measured feature value for each subcellular component of the cell determined in step S40 (step S50). In the present embodiment, a plurality of feature values are calculated for a single cell. The feature values include a luminance value of a pixel, an area of a certain region present in an image, a distribution value of luminance of a pixel, and the like. The feature values include a plurality of types suitable for respective subcellular components of a cell. As an example, a feature value of an image of a cell nucleus includes a total luminance value within the nucleus, an area of the nucleus, and the like. A feature value of an image of cytoplasm includes a total luminance value within the cytoplasm, an area of the cytoplasm, and the like. In addition, a feature value of an image of the whole cell includes a total luminance value within the cell, an area of the cell, and the like. In addition, a feature value of an image of a mitochondrion includes a fragmentation rate. The feature value calculating unit 102 may normalize and calculate the feature value to a value between 0 (zero) and 1, for example.

In addition, the feature value calculating unit 102 may calculate the feature values based on information about stimulus applied to a cell associated with a cell image. For example, in the case of a cell image captured when a stimulus for causing an antibody to react with a cell is applied to the cell, the feature value calculating unit 102 may calculate a feature value specific to the case where the antibody is caused to react with the cell. In addition, in the case of a cell image captured when a cell is stained or a fluorescence protein is applied to the cell, the feature value calculating unit 102 may calculate a feature value specific to the case where the cell is stained or the fluorescence protein is applied to the cell. In these cases, the storage unit 200 may include an experimental condition storage unit 201. The experimental condition storage unit 201 stores information about experimental conditions for a cell associated with a cell image, for each cell image. The information about experimental conditions includes conditions of a cell, conditions in which an image is acquired, conditions of treatment to a cell, and the like, for example. The conditions of a cell include a type of cell; and whether the cell is a controlled cell or in an inhibited phase, for example. The conditions in which an image is acquired include imaging conditions such as a type of microscope device used, a magnification at the time of acquiring the image, and the like, for example. The conditions of treatment to a cell include staining conditions when the cell is stained, a type of stimulus applied to the cell, and the like, for example.

When the experimental condition storage unit 201 does not store experimental conditions, the experimental conditions may be input using an input unit 401. The input unit 401 includes a touch panel, a mouse, a keyboard, or the like, for example. In addition, when experimental conditions are not stored in the analysis device 10, information may be obtained from another device. For example, the microscope apparatus 20 may obtain information about the experimental conditions. In addition, information about the experimental conditions may be obtained from a public database or literature, for example. In this case, a type of cell included in a captured image may be identified by comparing the captured image with an image included in a public database or literature, and information about the type of cell may be used.

Calculation Result of Feature Value

Calculation results of feature values calculated by the feature value calculating unit 102 will be described with reference to FIG. 6.

Figure 6:
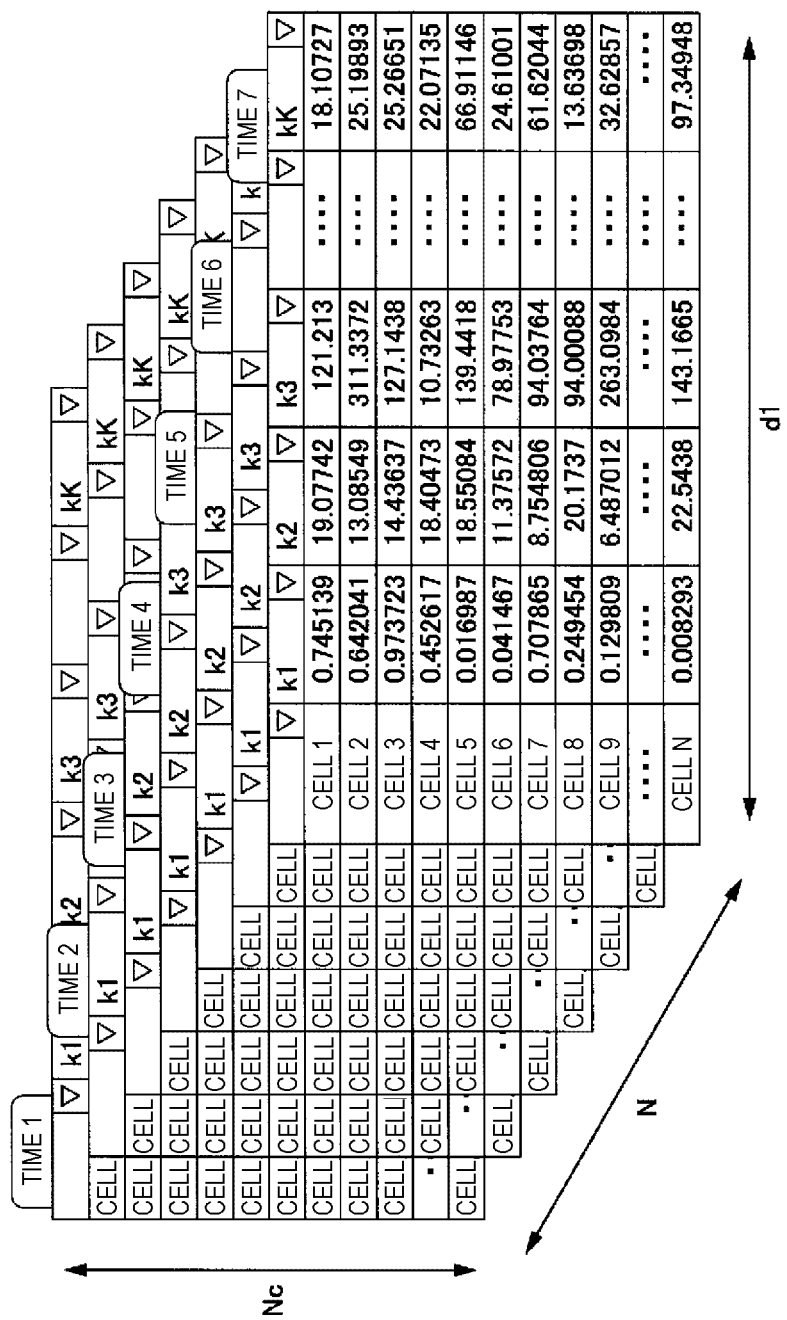
FIG. 6 is a diagram showing an example of calculation results of feature values calculated by a feature value calculating unit according to the present embodiment.

FIG. 6 is a diagram showing an example of calculation results of feature values calculated by the feature value calculating unit 102 according to the present embodiment. The feature value calculating unit 102 calculates a plurality of feature values for the cell CL for each subcellular component and for each time. In this example, the feature value calculating unit 102 calculates feature values of the number N of subcellular components from a subcellular component 1 to a subcellular component N. In this example, the feature value calculating unit 102 also calculates feature values for seven times from time 1 to time 7. In addition, in this example, the feature value calculating unit 102 also calculates K types of feature value from a feature value k1 to a feature value kK. That is, in this example, the feature value calculating unit 102 calculates the feature values in three axial directions. Here, an axis in a cell direction is referred to as an axis Nc, an axis in a time direction is referred to as an axis N, and an axis in a feature value direction is referred to as an axis d1.

The K types of feature value from the feature value k1 to the feature value kK are each a combination of feature values of a cell 1. Cells other than the cell 1 or subcellular components of the cells other than the cell 1 may be different in a type of feature value or a combination of feature values.

Returning to FIG. 5, the feature value calculating unit 102 feeds inhibited feature values and controlled feature values that are calculated in step S50 to the signal determining unit 103, the correlation calculating unit 104, the significant difference determining unit 105, and the difference calculating unit 106.

The analysis device 10 analyzes the attribute of the correlation between the subcellular component A and the subcellular component B (step S60). Specifically, the signal determining unit 103, the correlation calculating unit 104, the significant difference determining unit 105, and the difference calculating unit 106 each acquire the inhibited feature values and the controlled feature values from the feature value calculating unit 102.

The signal determining unit 103 performs the analyses of (1) and (2) described above. The correlation calculating unit 104 performs the analyses of (3) and (6) described above. The significant difference determining unit 105 performs the analysis of (4) described above. The difference calculating unit 106 performs the analysis of (5) described above.

The signal determining unit 103 feeds analytical results to the result integrating unit 107. The correlation calculating unit 104 feeds analytical results to the result integrating unit 107. The significant difference determining unit 105 feeds analytical results to the result integrating unit 107. The difference calculating unit 106 feeds analytical results to the result integrating unit 107.

Determination Whether There is Signal With reference to FIGS. 7 to 10, a method of calculating a signal from the subcellular component B described above will be described.

The analysis device 10 determines whether there is a signal from the subcellular component B based on a statistical test.

Figure 7:
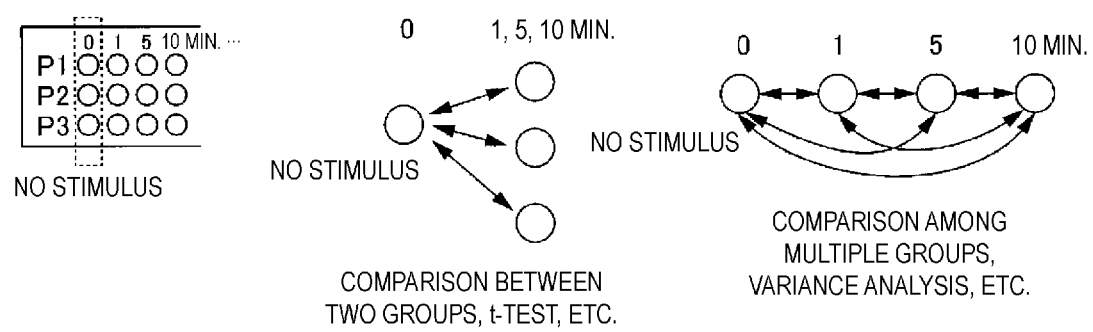
FIG. 7 is a diagram illustrating an example of comparison of feature values changing in a time-dependent manner in relation to a stimulus.

FIG. 7 is a diagram illustrating an example of comparison of feature values changing in a time-dependent manner in relation to a stimulus.

The analysis device 10 determines whether there is a signal by performing comparison between two groups or comparison among multiple groups. This comparison determines whether there is a signal, depending on whether two criteria of a p-value and an effect size each exceed a predetermined threshold. In addition, a group refers to a group of cells different in elapse of time after application of a stimulus. The predetermined threshold is calculated using a feature value of a non-stimulated cell. The non-stimulated cell refers to a cell before application of a stimulus. The threshold is determined using a non-stimulated cell before application of a stimulus. A plurality of non-stimulated cells may be used to determine the threshold.

Comparison between two groups refers to comparison between two feature values of a feature value at a predetermined time and a feature value at a time different from the predetermined time. The comparison between two groups also refers to comparison between feature values of a cell group at a predetermined time and feature values of the cell group at a time different from the predetermined time. For example, as shown in FIG. 7, the analysis device 10 compares a feature value before application of a stimulus (0 minute) with a feature value after an elapse of one minute from the application of a stimulus. Likewise, a feature value immediately after the application of a stimulus is compared with a feature value after an elapse of five minutes from the application of a stimulus. The comparison between two groups is performed according to t-test or the like. The t-test refers to a test of difference in average. The comparison between two groups is not limited to the t-test and may be performed by an F-test being a homoscedastic test, a two-sample Kolmogorov-Smirnov test, a Burnner-Munzel test, or the like. The analysis device 10 performs the comparison between two groups using the p-value and the effect size and determines that there is a signal when the two groups each have a feature value more than a predetermined threshold.

The comparison between two groups is effective in data that is not suitable for the comparison among multiple groups described above. For example, the cases include a case where the number of cells varies between groups including a group having fewer cells, and the like. In addition, the comparison between two groups is also suitable for a case where only one group has a change and the other group has less change.

The comparison among multiple groups is a test capable of performing comparison among groups different in elapse of time at once. For example, the analysis device 10 compares a feature value before application of a stimulus, the feature value after elapse of one minute from the application of the stimulus, the feature value after elapse of five minutes from the application of the stimulus, and the feature value after elapse of ten minutes from the application of the stimulus, in a round-robin manner. The comparison among multiple groups is performed by variance analysis, Kruskal-Wallis test, or the like. The analysis device 10 performs the comparison among multiple groups using the p-value and the effect size and determine that there is a signal when the feature value exceeds a predetermined threshold. Here, the predetermined threshold is calculated based on the feature value of the non-stimulated cell described above.

Figures 8A, 8B:
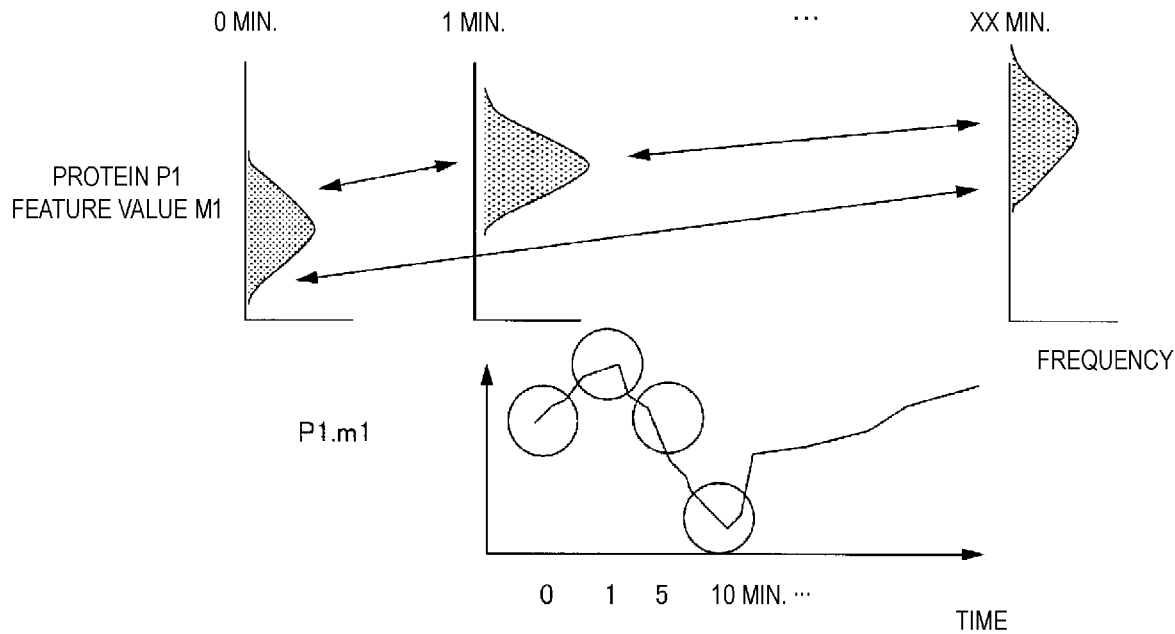
FIGS. 8A to 8B are a diagram illustrating an example of comparison among multiple groups.

FIGS. 8A to 8B are a diagram illustrating an example of the comparison among multiple groups.

FIG. 8A is a diagram illustrating an example of a feature value calculated from a non-stimulated cell. The analysis device 10 uses a maximum value of 0.202 of the effect size as a predetermined threshold. That is, the analysis device 10 determines that there is a signal when the effect size exceeds 0.202.

FIG. 8B is a diagram illustrating an example of a feature value calculated from a controlled cell or an inhibited cell. Feature values "P1. m1" and "P1. m3" each have an effect size less than a predetermined threshold, so they are each determined as "no signal". Feature values "P1. m2" and "P2. m1" each have an effect size more than the predetermined threshold, so they are each determined as "with signal".

FIGS. 9A to 9B are a diagram illustrating an example of the comparison between two groups and a signal determination result of the comparison among multiple groups. FIG. 9A shows results of the comparison among multiple groups. FIG. 9B shows results of the comparison between two groups. Here, while a feature value B2 is determined as "without signal" in the results of the comparison among multiple groups, the feature value B2 is compared as "with signal" in the results of the comparison between two groups. This is because a p-value_5 and an effect size_5 exceed the predetermined threshold in the comparison between two groups.

Next, details of step S60 in FIG. 5 will be described with reference to FIG. 10.

Figure 10:
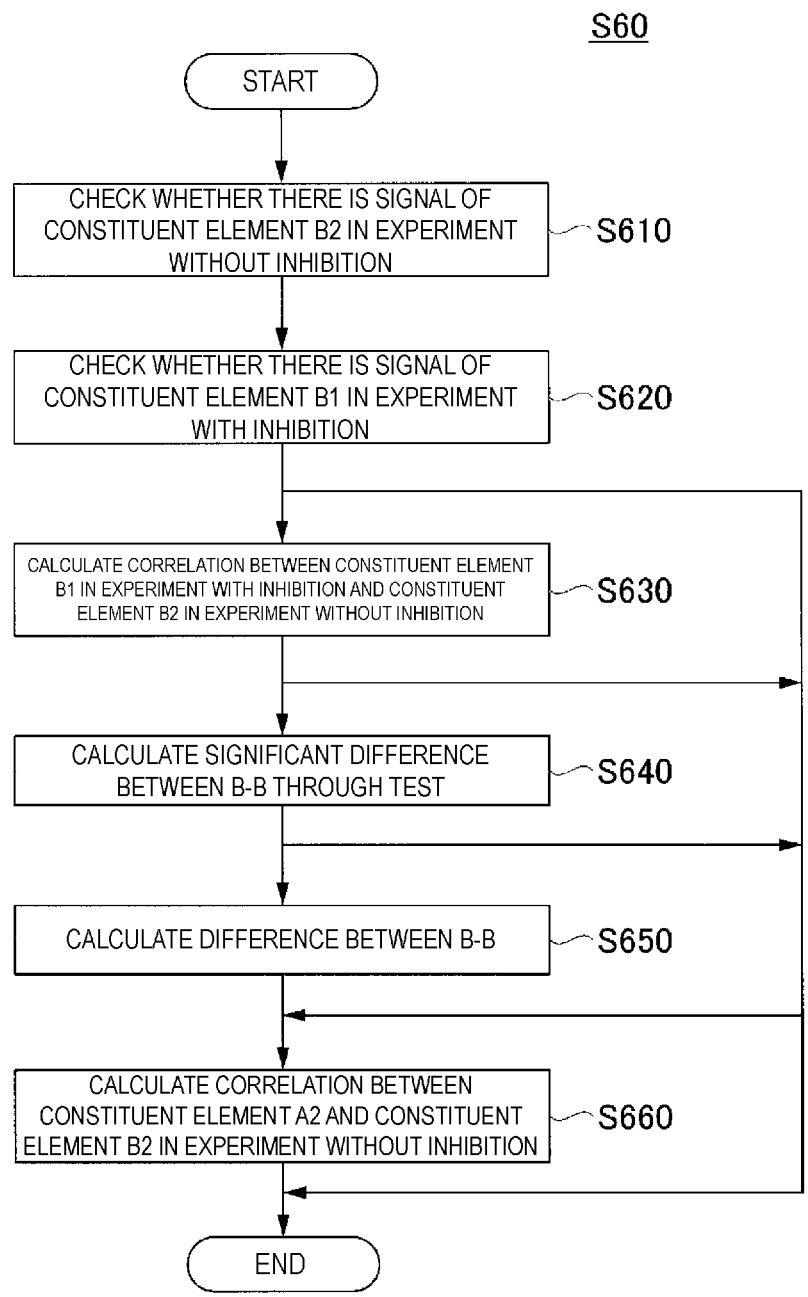
FIG. 10 is a flowchart illustrating an example of a detailed computation procedure of the arithmetic unit according to the present embodiment.

FIG. 10 is a flowchart illustrating an example of a detailed computation procedure of the arithmetic unit 100 according to the present embodiment. The computation procedure described here is an example, and the computation procedure may be eliminated, or another computation procedure may be added.

The signal determining unit 103, the correlation calculating unit 104, the significant difference determining unit 105, and the difference calculating unit 106 each determine whether there is a signal of the subcellular component B in an experiment without inhibition (step S610), and the signal determining unit 103, the correlation calculating unit 104, the significant difference determining unit 105, and the difference calculating unit 106 each determine whether there is a signal of the constituent B in an experiment with inhibition (step S620). The signal determining unit 103 performs the analyses of (1) and (2) described above based on the determination results.

FIGS. 11A to 11B are a diagram illustrating an example of a network based on a result determined by the signal determining unit 103.

FIG. 11A is a part of the Table shown in FIG. 4.

FIG. 11B is a network where there is no signal of the subcellular component B1 of a controlled cell and no signal of the subcellular component B2 of an inhibited cell. There is no response from the subcellular component B, so a node A indicating the subcellular component A and a node B indicating the subcellular component B are not connected with an edge.

FIG. 11C is a network when the subcellular component A activates the subcellular component B. An edge is drawn with an arrowhead in a direction from the node A to the node B. This indicates that the subcellular component A activates the subcellular component B.

FIG. 11D is a network where the subcellular component A inhibits the subcellular component B. In the direction from the node A to the node B, an edge in the shape of an inversed T is drawn. When it is preliminarily known that the subcellular component B is activated by the subcellular component C, an edge is drawn with an arrowhead in a direction from the node C to the node B.

The correlation calculating unit 104 performs the analysis of (3) described above by calculating a correlation between the subcellular component B1 and the subcellular component B2 with correlation analysis (step S630).

The correlation calculating unit 104 calculates the correlation between subcellular component B1 and subcellular component B2 with a method according to Graphical lasso (step S740). In the following description, the method according to Graphical lasso is also referred to as the Graphical Lasso method. In the present embodiment, a regularization parameter determined by the correlation calculating unit 104 is a regularization parameter used in the Graphical Lasso method. The Graphical Lasso method is an efficient algorithm for estimating a precision matrix from a L1-normalized Gaussian model. For example, refer to "Sparse inverse covariance estimation with the graphical lasso" in Biostatistics (2008), 9, 3 432-441, authored by JEROME FRIEDMAN, TREVOR HASTIE, and ROBERT TIBSHIRANI. The normalization parameter used in the Graphical Lasso method has a value more than 0 and less than 1. Besides this, the correlation is also calculated with Pearson product-moment correlation or the like, for example.

The correlation calculating unit 104 also performs the analysis of (6) described above by calculating a correlation between the subcellular component A1 and the subcellular component B1 with correlation analysis.

FIG. 12 is a diagram illustrating an example of a table of determination results of the correlation calculating unit 104, the significant difference determining unit 105, and the difference calculating unit 106.

Figure 13A:
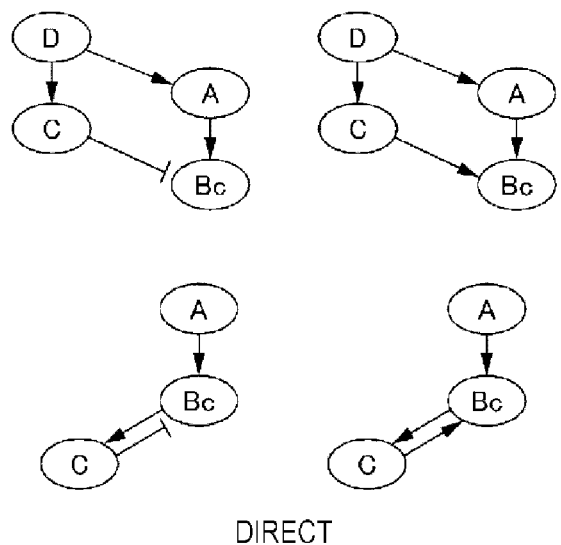
FIGS. 13A to 13B are a diagram illustrating an example of a network in a case of "direct" or "indirect" determined by the correlation calculating unit.
Figure 13B:
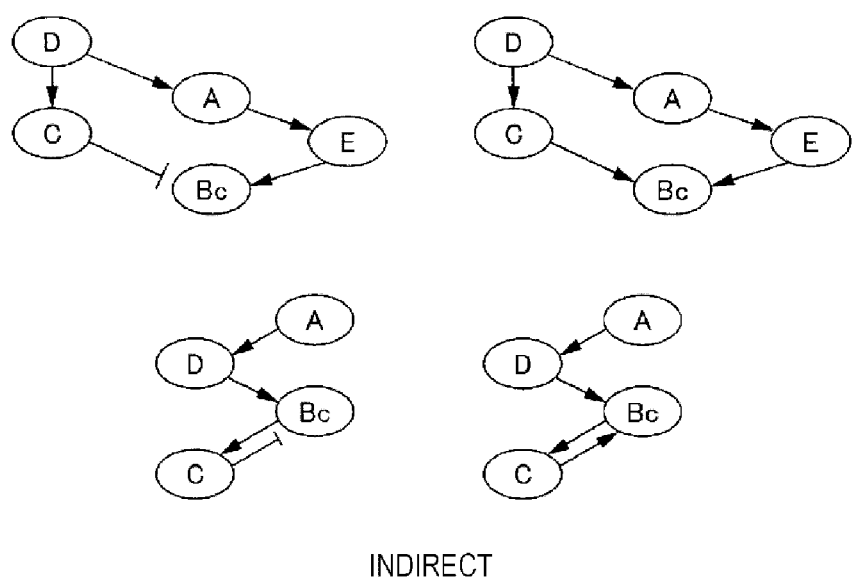

FIGS. 13A to 13B are a diagram illustrating an example of a network in a case of "direct" or "indirect" determined by the correlation calculating unit 104. FIG. 13A illustrates an example of a "direct" network. FIG. 13A illustrates that the node A and the node B are connected by an edge directly. An attribute of this edge is determined by other analyses (1) to (5). When a network between other subcellular components is preliminarily known, it may be described in the same network.

FIG. 13B illustrates an example of an "indirect" network. FIG. 13B illustrates that the node A and the node B are connected via another node. The connection via another node is determined by analyzing an attribute of a correlation between the subcellular component A and a subcellular component other than the subcellular component B.

The significant difference determining unit 105 performs the analysis of (4) described above by calculating a difference in a feature value between the subcellular component B1 and the subcellular component B2 (step S640).

Figure 14A:
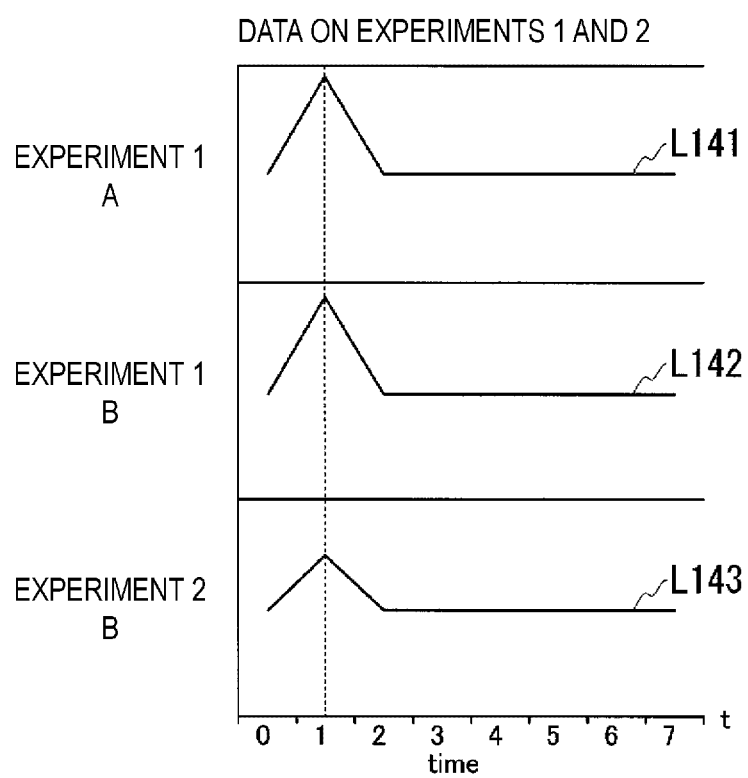
FIGS. 14A to 14C are a diagram illustrating an example of determination results of the significant difference determining unit.
Figures 14B, 14C:
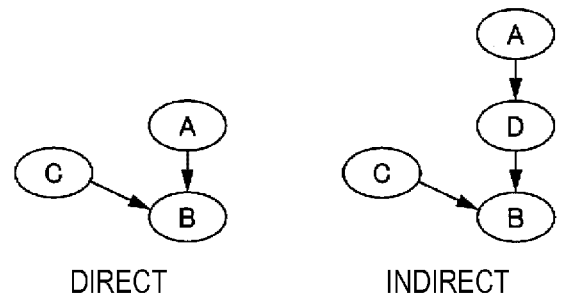

FIGS. 14A to 14C are a diagram illustrating an example of determination results of the significant difference determining unit 105.

FIG. 14A is a graph illustrating an example of changes over time of a controlled feature value and an inhibited feature value. A line L141 indicates a feature value of the subcellular component A1 included in the controlled feature value. This feature value is data in which luminance values of the subcellular component A1 are plotted in a time series manner, for example. A line L142 indicates a feature value of the subcellular component B1 included in the controlled feature value. A line L143 indicates a feature value of the subcellular component B2 included in the inhibited feature value.

The line L141, the line L142, and the line L143 are each the feature value with a peak of change at time t=1. In other words, the feature value of the subcellular component A1 included in the controlled feature value, the feature value of the subcellular component B1 included in the controlled feature value, and the feature value of the subcellular component B2 included in the inhibited feature value each have the same response time to a stimulus. That is, the subcellular component A1, the subcellular component B1, and the subcellular component B2 are correlated with each other.

The significant difference determining unit 105 determines whether there is a difference in height of the peak between the subcellular component B1 and the subcellular component B2. In this example, the feature value of subcellular component B1 and the feature value of subcellular component B2 differ in height of the peak. That is, the subcellular component B1 and the subcellular component B2 have a significant difference. Thus, the significant difference determining unit 105 determines that the subcellular component B is "downstream" of the subcellular component A. Based on this determination, a direction of an arrowhead of the edge between the node A and the node B is determined, such as networks shown in FIGS. 14B and 14C. In this case, the node B is downstream of the node A, so the edge is drawn with an arrow from the node A to the node B.

In addition, "direct" or "indirect" is determined by the analytical result of (6) calculated by the correlation calculating unit 104 described above.

In a case where the significant difference determining unit 105 determines that there is no significant difference between the subcellular component B1 and the subcellular component B2, the significant difference determining unit 105 determines the case as "non-downstream" as described above. Under the determination of "non-downstream", the analysis device 10 determines that the subcellular component B has "high possibility of being upstream" of the subcellular component A when results of (6) determined by the correlation calculating unit 104 indicate that there is a high correlation between the subcellular component A1 and the subcellular component B1. This shows that the subcellular component B may be influenced by another subcellular component other than the subcellular component A because a signal from the subcellular component B does not change regardless of that the subcellular component A is inhibited or not. The subcellular component B is less influenced by the subcellular component A because a signal of the subcellular component B has a high correlation with between the subcellular component A with inhibition and that without inhibition. In addition, the subcellular component A and the subcellular component B have a high correlation when there is without inhibition and there is no significant difference in a feature value between the subcellular component B1 and the subcellular component B2. Thus, the subcellular component B is considered upstream of the subcellular component A.

Figure 15A:
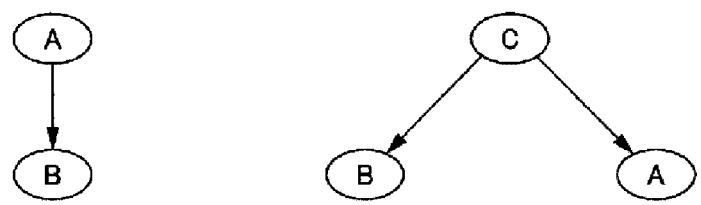
FIGS. 15A to 15B are a diagram illustrating an example of the network.
Figure 15B:
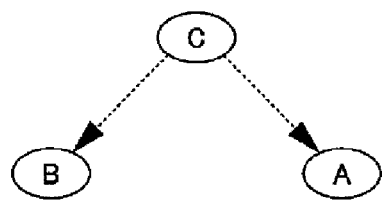

FIGS. 15A to 15B is a diagram illustrating an example of the network.

FIG. 15A is a network under determination of "high possibility of being upstream". FIG. 15B is a network under determination of "not downstream".

The difference calculating unit 106 performs the analysis of (5) described above by calculating a difference in a feature value between the subcellular component B1 and the subcellular component B2 (step S650).

Figure 16A:
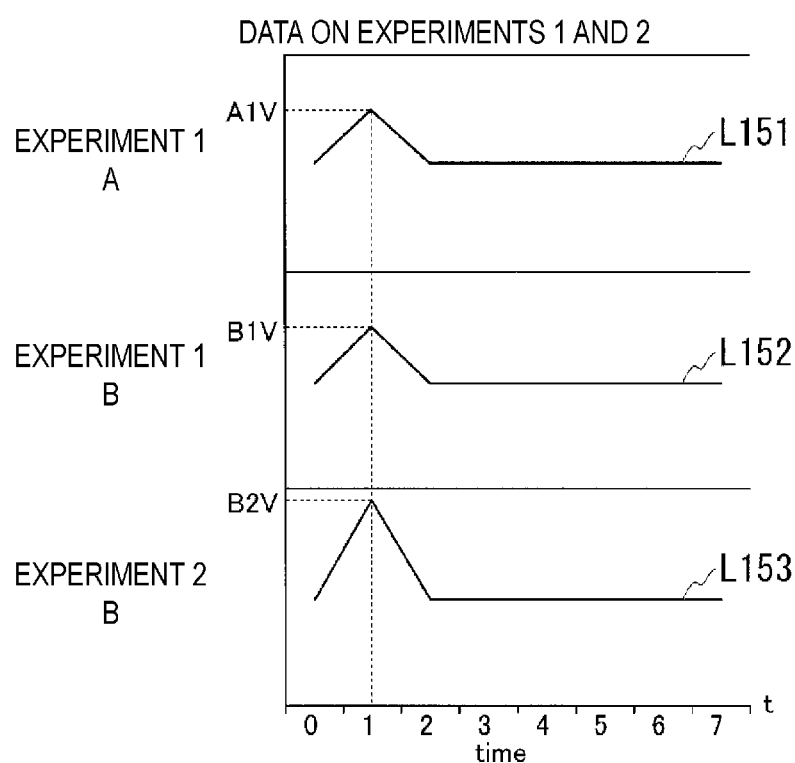
FIGS. 16A to 16C are a diagram illustrating an example of determination results of the difference calculating unit.
Figure 16B:
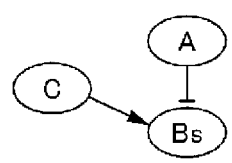
Figure 16C:
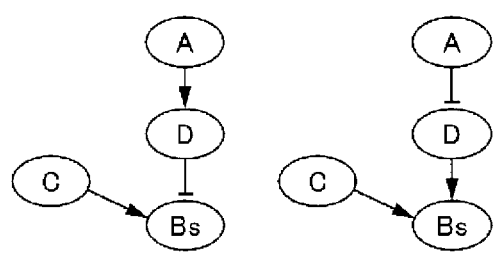

FIGS. 16A to 16C is a diagram illustrating an example of determination results of the difference calculating unit 106.

FIG. 16A is a graph illustrating an example of changes over time of a controlled feature value and an inhibited feature value. A line L151 indicates a feature value of the subcellular component A1 included in the controlled feature value. A line L152 indicates a feature value of the subcellular component B1 included in the controlled feature value. A line L153 is the feature value of subcellular component B2 included in the inhibited feature value.

The line L151, the line L152, and the line L153 are each the feature value with a peak at time t=1. That is, the subcellular component A1, the subcellular component B1, and the subcellular component B2 are correlated with each other.

The difference calculating unit 106 determines a difference in a peak value between the subcellular component B1 and the subcellular component B2.

In this example, the feature value of the subcellular component B1 has a peak of a value B1V. The feature value of the subcellular component B2 has a peak of a value B2V. The value B2V is more than the value B1V. The subcellular component B2 has a peak more than the subcellular component B1. Thus, the difference calculating unit 106 determines that the subcellular component B is "oddly suppressed" by the subcellular component A.

Based on this determination result, a direction of an arrowhead of an edge between the node A and the node B is determined, such as networks shown in FIGS. 16B and 16C. In this case, the node B is downstream of the node A, so the edge is drawn with an arrow from the node A to the node B.

In addition, "direct" or "indirect" is determined by the analytical result of (6) calculated by the correlation calculating unit 104 described above.

The correlation calculating unit 104 performs the analysis of (6) described above by calculating a correlation between the subcellular component A1 and the subcellular component B1 with correlation analysis (step S660).

Computations from step S620 to step S660 described above may be performed as necessary, and all of the computations need not be performed.

Returning to FIG. 5, the result integrating unit 107 acquires the analytical results from each of the signal determining unit 103, the correlation calculating unit 104, the significant difference determining unit 105, and the difference calculating unit 106.

When the analytical result of (1) described above shows "without response" and the analytical result of (2) shows "no response", the result integrating unit 107 determines "no response" as a conclusion of the analytical results and as an analytical result of the arithmetic unit 100.

When the analytical result of (1) described above shows "without response" and the analytical result of (2) shows "suppression", the result integrating unit 107 determines "suppression" as a conclusion of the analytical results and as an analytical result of the arithmetic unit 100.

When the analytical result of (1) described above shows "with response" and the analytical result of (2) shows "activation", the result integrating unit 107 determines "activation" as a conclusion of the analytical results and as an analytical result of the arithmetic unit 100.

When the analytical result of (1) described above shows "with response", the analytical result of (2) shows "with response under inhibition", and the analytical result of (3) shows "different B-B response", the result integrating unit 107 determines "adjustment" as a conclusion of the analytical results and as an analytical result of the arithmetic unit 100.

When the analytical result of (1) described above shows "with response", the analytical result of (2) shows "with response under inhibition", the analytical result of (3) shows "opposite B-B response", the analytical result of (5) shows "reverse suppression", and the analytical result of (6) shows "low", the result integrating unit 107 determines "indirect reverse suppression" as a conclusion of the analytical results and as an analytical result of the arithmetic unit 100.

When the analytical result of (1) described above shows "with response", the analytical result of (2) shows "with response under inhibition", the analytical result of (3) shows "opposite B-B response", the analytical result of (5) shows "reverse suppression", and the analytical result of (6) shows "high", the result integrating unit 107 determines "direct reverse suppression" as a conclusion of the analytical results and as an analytical result of the arithmetic unit 100.

When the analytical result of (1) described above shows "with response", the analytical result of (2) shows "with response under inhibition", the analytical result of (3) shows "opposite B-B response", the analytical result of (5) shows "reverse activation", and the analytical result of (6) shows "low", the result integrating unit 107 determines "indirect reverse suppression" as a conclusion of the analytical results and as an analytical result of the arithmetic unit 100.

When the analytical result of (1) described above shows "with response", the analytical result of (2) shows "with response under inhibition", the analytical result of (3) shows "opposite B-B response", the analytical result of (5) shows "reverse activation", and the analytical result of (6) shows "high", the result integrating unit 107 determines "direct reverse activation" as a conclusion of the analytical results and as an analytical result of the arithmetic unit 100.

When the analytical result of (1) described above shows "with response", the analytical result of (2) shows "with response under inhibition", the analytical result of (3) shows "same B-B response", the analytical result of (4) shows "non-downstream", and the analytical result of (6) shows "low", the result integrating unit 107 determines "not downstream" as a conclusion of the analytical results and as an analytical result of the arithmetic unit 100. This indicates that the subcellular component A is not downstream of the subcellular component B.

When the analytical result of (1) described above shows "with response", the analytical result of (2) shows "with response under inhibition", the analytical result of (3) shows "same B-B response", the analytical result of (4) shows "non-downstream", and the analytical result of (6) shows "high", the result integrating unit 107 determines "the subcellular component B having a high possibility of being upstream of the subcellular component A" as a conclusion of the analytical results and as an analytical result of the arithmetic unit 100.

When the analytical result of (1) described above shows "with response", the analytical result of (2) shows "with response under inhibition", the analytical result of (3) shows "same B-B response", the analytical result of (4) shows "downstream", the analytical result of (5) shows "oddly suppressed", and the analytical result of (6) shows "low", the result integrating unit 107 determines "oddly and indirectly suppressed" as a conclusion of the analytical results and as an analytical result of the arithmetic unit 100.

When the analytical result of (1) described above shows "with response", the analytical result of (2) shows "with response under inhibition", the analytical result of (3) shows "same B-B response", the analytical result of (4) shows "downstream", the analytical result of (5) shows "oddly suppressed", and the analytical result of (6) shows "high", the result integrating unit 107 determines "oddly and directly suppressed" as a conclusion of the analytical results and as an analytical result of the arithmetic unit 100.

When the analytical result of (1) described above shows "with response", the analytical result of (2) shows "with response under inhibition", the analytical result of (3) shows "same B-B response", the analytical result of (4) shows "downstream", the analytical result of (5) shows "oddly activated", and the analytical result of (6) shows "low", the result integrating unit 107 determines "oddly and indirectly activated" as a conclusion of the analytical results and as an analytical result of the arithmetic unit 100.

When the analytical result of (1) described above shows "with response", the analytical result of (2) shows "with response under inhibition", the analytical result of (3) shows "same B-B response", the analytical result of (4) shows "downstream", the analytical result of (5) shows "oddly activated", and the analytical result of (6) shows "high", the result integrating unit 107 determines "oddly and directly activated" as a conclusion of the analytical results and as an analytical result of the arithmetic unit 100.

The result integrating unit 107 generates a network or a list of results based on these integrated results. The result integrating unit 107 feeds the generated network or the generated list of results to the display image generating unit 108. The display image generating unit 108 acquires the network or the list of results from the result integrating unit 107. The display image generating unit 108 generates a display image based on the network or the list of results acquired from the result integrating unit 107 (step S70).

The display image generating unit 108 feeds the generated display image to the result output unit 300. The result output unit 300 acquires the display image from the display image generating unit 108. The result output unit 300 causes the display 30 to display the display image acquired from the result integrating unit 107 (step S80).

Detailed Analysis Method 1 for "Adjustment"

Next, with reference to FIG. 17, a method for analyzing an item determined as "adjustment" in the description above is described in detail in which the difference calculating unit 106 determines change over time in an inhibited feature value and a controlled feature value of the subcellular component B to a stimulus.

FIG. 17 is a diagram illustrating details of analysis of "adjustment" using the difference calculating unit 106.

When the difference calculating unit 106 determines that there is no correlation between the subcellular component B1 and the subcellular component B2 and determines a case as "different B-B response", the difference calculating unit 106 determines the case by dividing feature values plotted in a time series manner into an "early period", a "middle period", and a "later period". While the time is divided into the three periods in this example, the number of periods divided is not limited thereto, and one time may be assigned to one period of time, or multiple times may be assigned to one period of time.

The "early period" is from time t=1 to time t=2. The "middle period" is from time t=3 to time t=5. The "later period" is from time t=6 to time t=7.

A line L171 indicates a controlled feature value. A line L172 indicates an inhibited feature value.

The difference calculating unit 106 calculates a difference between a feature value at a reference point CP1 and a feature value corresponding to the "early period" in the line L171. In this example, the difference between the feature value at the reference point CP1 and the feature value corresponding to the "early period" is a "positive" difference. The difference calculating unit 106 also calculates a difference between a feature value at a reference point CP2 and a feature value corresponding to the "early period" in the line L172. In this example, the difference between the feature value at the reference point CP2 and the feature value corresponding to the "early period" is nothing and is referred to as "nothing". The difference calculating unit 106 determines the result in the early period as "compensation suppression" that is a result indicated by "positive, nothing".

Here, while the reference point CP1 and the reference point CP2 each may be a feature value at any time or a value determined by a user, a feature value before application of a stimulus is preferably used for them.

Likewise, the difference calculating unit 106 determines each of the "middle period" and the "later period". In this example, the result in the "middle period" is determined as "no response" that is a result indicated by "nothing, nothing". The result in the "later period" is determined as "reverse suppression" that is a result indicated by "negative, positive".

When differences in the controlled feature value and the inhibited feature value are calculated as "nothing, nothing" in the order described above, the difference calculating unit 106 determines the subcellular component B as "no response".

Likewise, when differences are calculated as "nothing, positive", the difference calculating unit 106 determines that the subcellular component B is "compensation suppression" by the subcellular component A.

Likewise, when differences are calculated as "nothing, negative", the difference calculating unit 106 determines that the subcellular component B is "compensation activation" by the subcellular component A.

Likewise, when differences are calculated as "positive, positive", the difference calculating unit 106 determines that the subcellular component B is "not influenced".

Likewise, when differences are calculated as "positive, nothing", the difference calculating unit 106 determines that the subcellular component B is "activation" by the subcellular component A.

Likewise, when differences are calculated as "positive, negative", the difference calculating unit 106 determines that the subcellular component B is "reverse activation" by the subcellular component A.

Likewise, when differences are calculated as "negative, negative", the difference calculating unit 106 determines that the subcellular component B is "not influenced".

Likewise, when differences are calculated as "negative, positive", the difference calculating unit 106 determines that the subcellular component B is "reverse suppression" by the subcellular component A.

Likewise, when differences are calculated as "negative, nothing", the difference calculating unit 106 determines that the subcellular component B is "suppression" by the subcellular component A.

Next, a computation procedure of the difference calculating unit 106 to analyze an item determined as "adjustment" in detail will be described with reference to FIG. 18.

Figure 18:
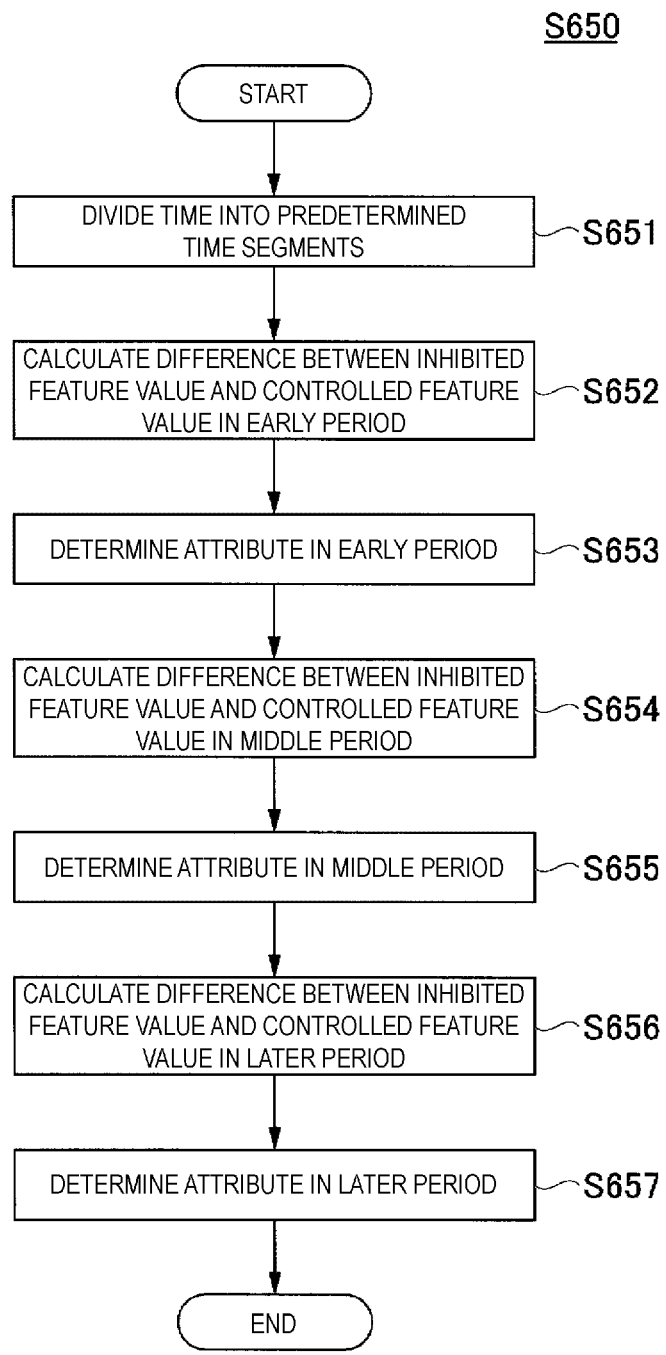
FIG. 18 is a flowchart illustrating an example of a computation procedure of the difference calculating unit to analyze an item determined as "adjustment" in detail.

FIG. 18 is a flowchart illustrating an example of the computation procedure of the difference calculating unit 106 to analyze an item determined as "adjustment" in detail.

The difference calculating unit 106 divides an inhibited feature value and a controlled feature value into predetermined time segments (step S651). In this example, the difference calculating unit 106 divides them into three segments of an "early period", a "middle period", and a "later period".

The difference calculating unit 106 calculates a difference between the controlled feature value corresponding to the "early period" and the reference point CP1. The difference calculating unit 106 calculates a difference between the inhibited feature value corresponding to the "early period" and a value at the reference point CP2 (step S652). Based on the calculated two differences, the difference calculating unit 106 determines an attribute of a correlation in the "early period" (step S653).

The difference calculating unit 106 calculates a difference between the controlled feature value corresponding to the "middle period" and the reference point CP1. The difference calculating unit 106 calculates a difference between the inhibited feature value corresponding to the "middle period" and the value at the reference point CP2 (step S654). Based on the calculated two differences, the difference calculating unit 106 determines an attribute of a correlation in the "middle period" (step S655).

The difference calculating unit 106 calculates a difference between the controlled feature value corresponding to the "later period" and the reference point CP1. The difference calculating unit 106 calculates a difference between the inhibited feature value corresponding to the "later period" and the value at the reference point CP2 (step S656). Based on the calculated two differences, the difference calculating unit 106 determines an attribute of a correlation in the "later period" (step S657).

Detailed Analysis Method 2 for "Adjustment"

In the detailed analysis method 1 for "adjustment", there is described a method of analyzing details of "adjustment" by calculating a difference between controlled feature values and a difference between inhibited feature values. Next, there will be described a method of analyzing details of "adjustment" by comparing a significant difference between an inhibited feature value and a controlled feature value.

The significant difference determining unit 105 analyzes the details by determining change over time in an inhibited feature value and a controlled feature value of the subcellular component B to a stimulus.

Figure 19:
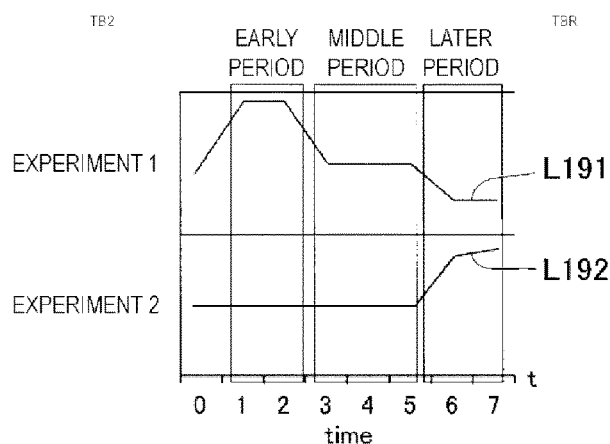
FIG. 19 is a diagram showing details of analysis of "adjustment" using the significant difference determining unit.

FIG. 19 is a diagram showing details of analysis of "adjustment" using the significant difference determining unit 105.

When the significant difference determining unit 105 determines a case as "different B-B response" due to no correlation between the subcellular component B1 and the subcellular component B2, the significant difference determining unit 105 divides time into an "early period", a "middle period", and a "later period" as described above to perform determination. The significant difference determining unit 105 determines a significant difference between a controlled feature value and an inhibited feature value corresponding to each of the "early period", the "middle period", and the "later period". While the time is divided into the three periods in this example, the number of periods divided is not limited thereto, and one time may be assigned to one period of time, or multiple times may be assigned to one period of time. When one period of time includes multiple times, a significant difference is determined by grouping controlled feature values and inhibited feature values into one group for each period.

A line L191 indicates a controlled feature value. A line L192 indicates an inhibited feature value.

The significant difference determining unit 105 determines a significant difference between the line L191 and the line L192 using feature values corresponding to each of the "early period", the "middle period", and the "later period". In this example, in the "early period", the controlled feature value is more than the inhibited feature value. In the "middle period", there is no difference between the controlled feature value and the inhibited feature value. In the "later period", the controlled feature value is less than the inhibited feature value. The significant difference determining unit 105 determines this case as "activation in early period, suppression in later period".

When the controlled feature value is more than the inhibited feature value in the "early period", the significant difference determining unit 105 determines that the subcellular component B is "activation" by the subcellular component A as a result in the "early period".

When there is no difference between the controlled feature value and the inhibited feature value in the "early period", the significant difference determining unit 105 determined that the subcellular component B is "not influenced" as a result in the "early period".

When the controlled feature value is less than the inhibited feature value in the "early period", the significant difference determining unit 105 determines that the subcellular component B is "suppression" by the subcellular component A as a result in the "early period".

Likewise, the significant difference determining unit 105 performs determination for the "middle period" and the "later period" with the determination method performed for the "early period".

In a case where the "early period" is determined as "activation", the "middle period" is determined as "activation", and the "later period" is determined as "activation", the significant difference determining unit 105 determines the case as "activation in all periods", as a conclusion of results.

In a case where the "early period" is determined as "activation", the "middle period" is determined as "activation", and the "later period" is determined as "not influenced", the significant difference determining unit 105 determines the case as "activation in early and middle periods", as a conclusion of results.

In a case where the "early period" is determined as "activation", the "middle period" is determined as "activation", and the "later period" is determined as "suppression", the significant difference determining unit 105 determines the case as "activation in early and middle periods, suppression in later period", as a conclusion of results.

In a case where the "early period" is determined as "activation", the "middle period" is determined as "not influenced", and the "later period" is determined as "activation", the significant difference determining unit 105 determines the case as "activation in early and later periods", as a conclusion of results.

In a case where the "early period" is determined as "activation", the "middle period" is determined as "not influenced", and the "later period" is determined as "not influenced", the significant difference determining unit 105 determines the case as "activation in early period", as a conclusion of results.

In a case where the "early period" is determined as "activation", the "middle period" is determined as "not influenced", and the "later period" is determined as "suppression", the significant difference determining unit 105 determines the case as "activation in early period, suppression in later period", as a conclusion of results.

In a case where the "early period" is determined as "activation", the "middle period" is determined as "suppression", and the "later period" is determined as "activation", the significant difference determining unit 105 determines the case as "activation in early and later periods, suppression in middle period", as a conclusion of results.

In a case where the "early period" is determined as "activation", the "middle period" is determined as "suppression", and the "later period" is determined as "not influenced", the significant difference determining unit 105 determines the case as "activation in early period, suppression in middle period", as a conclusion of results.

In a case where the "early period" is determined as "activation", the "middle period" is determined as "suppression", and the "later period" is determined as "suppression", the significant difference determining unit 105 determines the case as "activation in early period, suppression in middle and later periods", as a conclusion of results.

In a case where the "early period" is determined as "not influenced", the "middle period" is determined as "activation", and the "later period" is determined as "activation", the significant difference determining unit 105 determines the case as "activation in middle and later periods", as a conclusion of results.

In a case where the "early period" is determined as "not influenced", the "middle period" is determined as "activation", and the "later period" is determined as "not influenced", the significant difference determining unit 105 determines the case as "activation in middle period", as a conclusion of results.

In a case where the "early period" is determined as "not influenced", the "middle period" is determined as "activation", and the "later period" is determined as "suppression", the significant difference determining unit 105 determines the case as "activation in middle period, suppression in later period", as a conclusion of results.

In a case where the "early period" is determined as "not influenced", the "middle period" is determined as "not influenced", and the "later period" is determined as "activation", the significant difference determining unit 105 determines the case as "activation in later period", as a conclusion of results.

In a case where the "early period" is determined as "not influenced", the "middle period" is determined as "not influenced", and the "later period" is determined as "not influenced", the significant difference determining unit 105 determines the case as "no relation", as a conclusion of results.

In a case where the "early period" is determined as "not influenced", the "middle period" is determined as "not influenced", and the "later period" is determined as "suppression", the significant difference determining unit 105 determines the case as "suppression in later period", as a conclusion of results.

In a case where the "early period" is determined as "not influenced", the "middle period" is determined as "suppression", and the "later period" is determined as "activation", the significant difference determining unit 105 determines the case as "suppression in middle period, activation in later period", as a conclusion of results.

In a case where the "early period" is determined as "not influenced", the "middle period" is determined as "suppression", and the "later period" is determined as "not influenced", the significant difference determining unit 105 determines the case as "suppression in middle period", as a conclusion of results.

In a case where the "early period" is determined as "not influenced", the "middle period" is determined as "suppression", and the "later period" is determined as "suppression", the significant difference determining unit 105 determines the case as "suppression in later, middle, and later periods", as a conclusion of results.

In a case where the "early period" is determined as "suppression", the "middle period" is determined as "activation", and the "later period" is determined as "activation", the significant difference determining unit 105 determines the case as "suppression in early period, activation in middle and later periods", as a conclusion of results.

In a case where the "early period" is determined as "suppression", the "middle period" is determined as "activation", and the "later period" is determined as "not influenced", the significant difference determining unit 105 determines the case as "suppression in early period, activation in middle period", as a conclusion of results.

In a case where the "early period" is determined as "suppression", the "middle period" is determined as "activation", and the "later period" is determined as "suppression", the significant difference determining unit 105 determines the case as "suppression in early and later periods, activation in middle period", as a conclusion of results.

In a case where the "early period" is determined as "suppression", the "middle period" is determined as "not influenced", and the "later period" is determined as "activation", the significant difference determining unit 105 determines the case as "suppression in early period, activation in later period", as a conclusion of results.

In a case where the "early period" is determined as "suppression", the "middle period" is determined as "not influenced", and the "later period" is determined as "not influenced", the significant difference determining unit 105 determines the case as "suppression in early period", as a conclusion of results.

In a case where the "early period" is determined as "suppression", the "middle period" is determined as "not influenced", and the "later period" is determined as "suppression", the significant difference determining unit 105 determines the case as "suppression in early and later periods", as a conclusion of results.

In a case where the "early period" is determined as "suppression", the "middle period" is determined as "suppression", and the "later period" is determined as "activation", the significant difference determining unit 105 determines the case as "suppression in early and middle periods, activation in later period", as a conclusion of results.

In a case where the "early period" is determined as "suppression", the "middle period" is determined as "suppression", and the "later period" is determined as "not influenced", the significant difference determining unit 105 determines the case as "suppression in early and middle periods", as a conclusion of results.

In a case where the "early period" is determined as "suppression", the "middle period" is determined as "suppression", and the "later period" is determined as "suppression", the significant difference determining unit 105 determines the case as "suppression in all periods", as a conclusion of results.

Next, a computation procedure of the significant difference determining unit 105 to analyze an item determined as "adjustment" in detail will be described with reference to FIG. 20.

Figure 20:
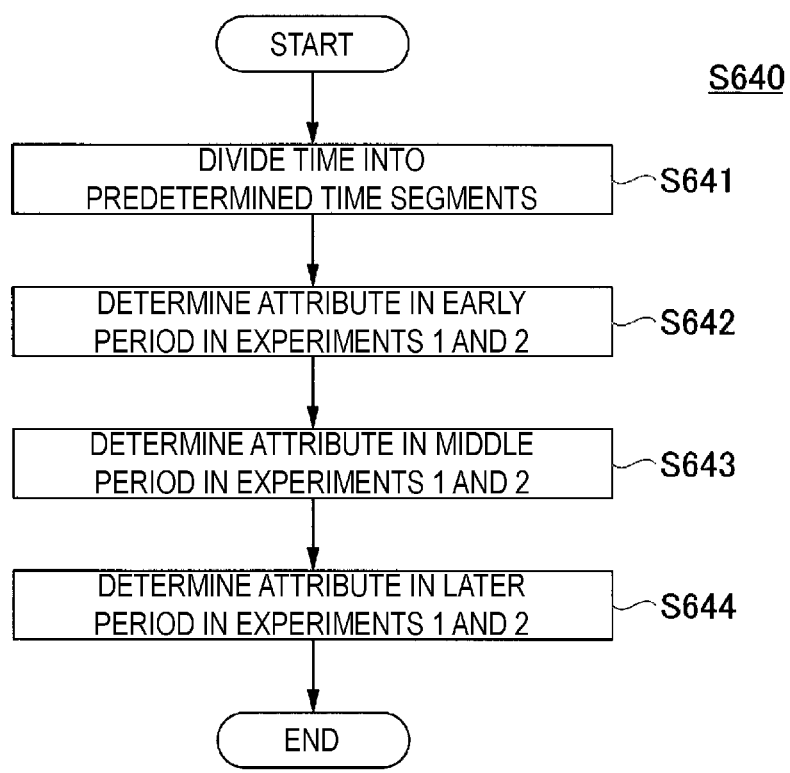
FIG. 20 is a flowchart illustrating an example of a computation procedure of the significant difference determining unit to analyze an item determined as "adjustment" in detail.

FIG. 20 is a flowchart illustrating an example of a computation procedure of the significant difference determining unit 105 to analyze an item determined as "adjustment" in detail.

The significant difference determining unit 105 divides an inhibited feature value and a controlled feature value into predetermined time segments (step S641). In this example, the difference calculating unit 106 divides them into three segments of an "early period", a "middle period", and a "later period".

The significant difference determining unit 105 determines a significant difference between a controlled feature value and an inhibited feature value corresponding to the "early period". Based on this determination result of the significant difference, the significant difference determining unit 105 determines an attribute of a correlation in the "early period" (step S642).

The significant difference determining unit 105 determines a significant difference between a controlled feature value and an inhibited feature value corresponding to the "middle period". Based on this determination result of the significant difference, the significant difference determining unit 105 determines an attribute of a correlation in the "middle period" (step S643).

The significant difference determining unit 105 determines a significant difference between a controlled feature value and an inhibited feature value corresponding to the "later period". Based on this determination result of the significant difference, the significant difference determining unit 105 determines an attribute of a correlation in the "later period" (step S644).

FIG. 21 is a diagram illustrating an example of a network between the subcellular component A and the subcellular component B based on a result determined by the significant difference determining unit 105.

This network shows that the subcellular component A activates the subcellular component B in the "early period", and the subcellular component A suppresses the subcellular component B in the "later period".

CONCLUSION

As described above, the analysis device 10 compares, an inhibited feature value acquired from an inhibited cell including a certain subcellular component that is inhibited, with, a controlled feature value acquired from a controlled cell including the certain subcellular component that is not inhibited, to analyze an attribute of a correlation between the certain subcellular component and another subcellular component different from the certain subcellular component.

This allows the analysis device 10 to analyze a relation of a correlation between subcellular components in addition to a conventional network configured to indicate that there is a correlation between a subcellular component and another subcellular component. For example, the analysis device 10 may analyze whether a subcellular component activates or inhibits another subcellular component. In addition, the analysis device 10 is capable of generating a display image showing a network or a list representing the analytical results. This allows the analysis device 10 to notify a user of an attribute of a correlation between subcellular components of a cell.

The analysis device 10 analyzes an attribute based on a plurality of determination results by combining the six analyses including: (1) an analysis of whether there is a signal of the subcellular component B of a controlled experimental result; (2) an analysis of whether there is a signal of the subcellular component B based on a controlled experimental result and an inhibited experimental result; (3) an analysis of whether feature values between B-B change at the same timing; (4) an analysis of whether variations in the feature values between B-B are different from each other; (5) an analysis of the variations in the feature values between B-B; and (6) an analysis of a controlled experimental result based on the correlation between the subcellular component A and the subcellular component B. Thus, the analysis device 10 is capable of analyzing the attribute of the correlation between the subcellular component A and the subcellular component B in detail.

In addition, the analysis device 10 determines whether there is a signal from a subcellular component by comparison among multiple groups or comparison between two groups. This allows the analysis device 10 to remove a signal such as a noise, so the analysis device 10 can more accurately analyze the attribute of the correlation between the subcellular component A and the subcellular component B.

While in the description above, the analysis device 10 is described about the attribute of the correlation between the subcellular component A and the subcellular component B, the present invention is not limited thereto. Other subcellular components acquired from inhibited experimental results and controlled experimental results may also be analyzed. For example, the analysis device 10 may analyze an attribute of a correlation between the subcellular component C included in the cell CL and the subcellular component A. The analysis device 10 may also combine, the attribute of the correlation between subcellular component A and the subcellular component B, with, the attribute of the correlation between the subcellular component A and the subcellular component C, to display the combined attribute.

An image to be processed by the analysis device 10 is not limited to an image captured by the microscope apparatus 20 and may be an image preliminarily stored in the storage unit 200 provided in the analysis device 10 or may be an image preliminarily stored in an external storage device (not illustrated), for example. That is, the analysis device 10 may not include the cell image acquiring unit 101. In addition, the microscope observation system 1 may not include the microscope apparatus 20.

An image to be fed to the analysis device 10 may be transmitted via a network such as the Internet or a communication line such as a telephone line. In addition, a single processor or a plurality of processors may be used to perform each processing of the analysis device 10. When a plurality of processors is used, processing may be performed by a processor different for each processing.

The various kinds of processing described above may be performed by storing a program for executing each processing of the analysis device 10 according to the embodiment of the present invention in a computer-readable storage medium and allowing a computer system to read and execute the program stored in the storage medium.

The "computer system" described above may include an OS and hardware such as a peripheral device. In addition, when the "computer system" uses a WWW system, the computer system also includes a homepage provision environment (or a display environment). In addition, a "recording medium that can be read by a computer" refers to a writable non-volatile memory such as a flexible disk, a magneto-optical disk, a ROM, or a flash memory; a portable recording medium such as a CD-ROM; or a storage device such as a hard disk built into the computer system.

Further, the "recording medium that can be read by a computer" may also include a medium holding a program for a certain period of time, such as a volatile memory (a Dynamic Random Access Memory (DRAM), for example) built into a computer system serving as a server or a client when the program is transmitted over a network such as the Internet or a communication line such as a phone line. In addition, the above-described program may be transmitted, from the computer system in which the program is stored in a storage device or the like, to another computer system, via a transmission medium or by a transmission wave in the transmission medium. Here, the "transmission medium" via which the program is transmitted refers to a medium having a function to transmit information, such as the Internet or another network (communication network), and a communication line such as a telephone line. In addition, the above-described program may be a program for executing a portion of the above-described functions. Further, the above-described program may be a so-called differential file (differential program) that can execute the above-described functions by a combination with a program having already recorded in the computer system.

The embodiments of the present invention are described above in detail with reference to the drawings, but a specific configuration is not limited to the embodiments, and designs and the like within the scope of the present invention are included.

Note that various aspects of the embodiments described above can be combined as appropriate. In addition, some of the components may be removed. In addition, to the extent permissible by law, all publications and US patent documents related to the devices or the like used in the embodiments and the modification examples as described above are incorporated herein by reference.

REFERENCE SIGNS LIST

1 Microscope observation system
10 Analysis device
20 Microscope apparatus
30 Display
101 Cell image acquiring unit
102 Feature value calculating unit
103 Signal determining unit
104 Correlation calculating unit
105 Significant difference determining unit
106 Difference calculating unit
107 Result integrating unit
108 Display image generating unit
200 Storage unit
300 Result output unit

The invention claimed is:

1. An analysis device configured to analyze an attribute of a correlation between responses to a stimulus to a first subcellular component that is a subcellular component of a cell and a second subcellular component different from the first subcellular component, the analysis device comprising:
an attribute analysis unit that analyzes the attribute of the correlation between the first subcellular component and the second subcellular component based on a first change in a feature value of the second subcellular component with respect to the stimulus in a state a function of the first subcellular component is suppressed and a second change in the feature value of the second subcellular component with respect to the stimulus in a state the function of the first subcellular component is not suppressed, wherein
a response time with respect to the stimulus of a third change in a feature value of the first subcellular component with respect to the stimulus is identical to a response time with respect to the stimulus of the second change.

2. The analysis device according to claim 1, wherein the attribute analysis unit analyzes the attribute of the correlation between the first subcellular component and the second subcellular component based on a difference between the first change and the second change.

3. The analysis device according to claim 1, wherein the attribute analysis unit analyzes the attribute of the correlation between the first subcellular component and the second subcellular component based on a difference between a variation of the first change and a variation of the second change.

4. An analysis device configured to analyze an attribute of a correlation between responses to a stimulus to a first subcellular component that is a subcellular component of a cell and a second subcellular component different from the first subcellular component, the analysis device comprising:
an attribute analysis unit that analyzes the attribute of the correlation between the first subcellular component and the second subcellular component based on a first change in a feature value of the second subcellular component with respect to the stimulus in a state a function of the first subcellular component is suppressed and a second change in the feature value of the second subcellular component with respect to the stimulus in a state the function of the first subcellular component is not suppressed, wherein
the attribute of the correlation is analyzed based on strength of a correlation between the feature value of the first subcellular component and the feature value of the second subcellular component.

5. An analysis device configured to analyze an attribute of a correlation between responses to a stimulus to a first subcellular component that is a subcellular component of a cell and a second subcellular component different from the first subcellular component, the analysis device comprising:
an attribute analysis unit that analyzes the attribute of the correlation between the first subcellular component and the second subcellular component based on a first change in a feature value of the second subcellular component with respect to the stimulus in a state a function of the first subcellular component is suppressed and a second change in the feature value of the second subcellular component with respect to the stimulus in a state the function of the first subcellular component is not suppressed, wherein
the attribute of the correlation is at least one of (i) an order of activation of the first subcellular component and the second subcellular component due to the stimulus, (ii) a state of activation of the first subcellular component and the second subcellular component due to the stimulus, and (iii) a causal relationship between the first subcellular component and the second subcellular component with respect to the stimulus.

6. The analysis device of claim 1, wherein the first change and the second change are each a change over time in the feature value of the second subcellular component with respect to the stimulus.

7. An analysis device configured to analyze an attribute of a correlation between responses to a stimulus to a first subcellular component that is a subcellular component of a cell and a second subcellular component different from the first subcellular component, the analysis device comprising:
an attribute analysis unit that analyzes the attribute of the correlation between the first subcellular component and the second subcellular component based on a first change in a feature value of the second subcellular component with respect to the stimulus in a state a function of the first subcellular component is suppressed and a second change in the feature value of the second subcellular component with respect to the stimulus in a state the function of the first subcellular component is not suppressed, wherein
the first change is calculated based on comparison of instances of the feature value that change in a time-dependent manner with respect to the stimulus.

8. The analysis device according to claim 7, wherein
the comparison is performed by comparing the instances of (i) the feature value at a predetermined time and (ii) the feature value at a time different from the predetermined time.

9. The analysis device according to claim 7, wherein
the comparison is performed by comparing at once the instances of feature values each measured after a different elapse of time.

10. A non-transitory computer readable medium storing thereon an analysis program for causing a computer, provided in an analysis device, to perform an analysis method for analyzing an attribute of a correlation between responses with respect to a stimulus to a first subcellular component that is a subcellular component of a cell and a second subcellular component different from the first subcellular component, the analysis method comprising:
an attribute analysis step of analyzing the attribute of the correlation between the first subcellular component and the second subcellular component based on a first change in a feature value of the second subcellular component with respect to the stimulus in a state a function of the first subcellular component is suppressed and a second change in the feature value of the second subcellular component with respect to the stimulus in a state the function of the first subcellular component is not suppressed, wherein
a response time with respect to the stimulus of a third change in a feature value of the first subcellular component with respect to the stimulus is identical to a response time with respect to the stimulus of the second change.

11. A non-transitory computer readable medium storing thereon an analysis program for causing a computer, provided in an analysis device, to perform an analysis method for analyzing an attribute of a correlation between responses with respect to a stimulus to a first subcellular component that is a subcellular component of a cell and a second subcellular component different from the first subcellular component, the analysis method comprising:
an attribute analysis step of analyzing the attribute of the correlation between the first subcellular component and the second subcellular component based on a first change in a feature value of the second subcellular component with respect to the stimulus in a state a function of the first subcellular component is suppressed and a second change in the feature value of the second subcellular component with respect to the stimulus in a state the function of the first subcellular component is not suppressed, wherein
the attribute of the correlation is analyzed based on strength of a correlation between the feature value of the first subcellular component and the feature value of the second subcellular component.

12. A non-transitory computer readable medium storing thereon an analysis program for causing a computer, provided in an analysis device, to perform an analysis method for analyzing an attribute of a correlation between responses with respect to a stimulus to a first subcellular component that is a subcellular component of a cell and a second subcellular component different from the first subcellular component, the analysis method comprising:
an attribute analysis step of analyzing the attribute of the correlation between the first subcellular component and the second subcellular component based on a first change in a feature value of the second subcellular component with respect to the stimulus in a state a function of the first subcellular component is suppressed and a second change in the feature value of the second subcellular component with respect to the stimulus in a state the function of the first subcellular component is not suppressed, wherein
the attribute of the correlation is at least one of (i) an order of activation of the first subcellular component and the second subcellular component due to the stimulus, (ii) a state of activation of the first subcellular component and the second subcellular component due to the stimulus, and (iii) a causal relationship between the first subcellular component and the second subcellular component with respect to the stimulus.

13. A non-transitory computer readable medium storing thereon an analysis program for causing a computer, provided in an analysis device, to perform an analysis method for analyzing an attribute of a correlation between responses with respect to a stimulus to a first subcellular component that is a subcellular component of a cell and a second subcellular component different from the first subcellular component, the analysis method comprising:
an attribute analysis step of analyzing the attribute of the correlation between the first subcellular component and the second subcellular component based on a first change in a feature value of the second subcellular component with respect to the stimulus in a state a function of the first subcellular component is suppressed and a second change in the feature value of the second subcellular component with respect to the stimulus in a state the function of the first subcellular component is not suppressed, wherein
the first change is calculated based on comparison of instances of the feature value that change in a time-dependent manner with respect to the stimulus.

* * * * *